US009388093B2

(12) United States Patent
Luo et al.

(10) Patent No.: US 9,388,093 B2
(45) Date of Patent: Jul. 12, 2016

(54) NOZZLE DESIGN FOR IONIC LIQUID CATALYZED ALKYLATION

(71) Applicants: Huping Luo, Richmond, CA (US); Moinuddin Ahmed, Hercules, CA (US); Krishniah Parimi, Alamo, CA (US); Bong Kyu Chang, Novato, CA (US); Michael John Girgis, Richmond, CA (US); Donald Henry Mohr, Orinda, CA (US); Hye Kyung Cho Timken, Albany, CA (US)

(72) Inventors: Huping Luo, Richmond, CA (US); Moinuddin Ahmed, Hercules, CA (US); Krishniah Parimi, Alamo, CA (US); Bong Kyu Chang, Novato, CA (US); Michael John Girgis, Richmond, CA (US); Donald Henry Mohr, Orinda, CA (US); Hye Kyung Cho Timken, Albany, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 187 days.

(21) Appl. No.: 14/323,333

(22) Filed: Jul. 3, 2014

(65) Prior Publication Data
US 2016/0002125 A1  Jan. 7, 2016

(51) Int. Cl.
*C07C 2/00* (2006.01)
*C07C 2/02* (2006.01)
*C07C 2/04* (2006.01)
(Continued)

(52) U.S. Cl.
CPC . *C07C 2/62* (2013.01); *B01F 5/048* (2013.01); *B01F 5/0652* (2013.01); *B01J 19/24* (2013.01); *B01J 19/26* (2013.01); *C07C 2/08* (2013.01); *C07C 2/70* (2013.01); *C07C 4/06* (2013.01); *C07C 5/277* (2013.01); *C10G 29/205* (2013.01); *B01F 2015/0221* (2013.01); *B01J 2219/00103* (2013.01); *B01J 2219/24* (2013.01); *C07C 2527/06* (2013.01); *C10G 2300/4081* (2013.01)

(58) Field of Classification Search
CPC ................. C07C 2/00–2/10; C07C 2/54–2/62; C07C 2/64; C07C 2/66; C07C 2/70; C07C 2/72; C07C 4/00; C07C 4/02; C07C 4/06; C07C 5/22; C07C 5/2767; C07C 5/277; C07C 2527/06; B01F 5/048; B01F 5/0652; C10G 29/00; C10G 29/20; C10G 29/205; C10G 2300/40; C10G 2300/4081
See application file for complete search history.

(56) References Cited

U.S. PATENT DOCUMENTS 2,747,974 A    5/1956  Felger
3,133,128 A    5/1964  McDonald
(Continued)

FOREIGN PATENT DOCUMENTS

CN    203061076    7/2013
CN    203648 116   6/2014
JP    CH 609888    3/1979

OTHER PUBLICATIONS

Anonymous: "Venturi injector—Aquamerik—aquaculture & environtment", Oct. 24, 2006, XP055183785, URL:http://web.archive.org/web.20061024172911/http://ww.aquameriklcatalogue/produits.cgi?cate gory=oxygenation_injecteurstypeventuri& lg=eng, p. 1, top figure.

*Primary Examiner* — Natasha Young
(74) *Attorney, Agent, or Firm* — Susan M. Abernathy

(57) ABSTRACT

Systems for ionic liquid catalyzed hydrocarbon conversion comprise a reactor vessel, a mixing device in fluid communication with the reactor vessel, and at least one circulation loop in fluid communication with the reactor vessel and the mixing device. The mixing device may comprise an upper venturi, at least one feed injection component, and a lower venturi. Such systems may be used for ionic liquid catalyzed alkylation reactions. Processes for ionic liquid catalyzed hydrocarbon conversion are also disclosed.

43 Claims, 17 Drawing Sheets

| (51) | Int. Cl. | |
|---|---|---|
| | C07C 2/06 | (2006.01) |
| | C07C 2/08 | (2006.01) |
| | C07C 2/54 | (2006.01) |
| | C07C 2/56 | (2006.01) |
| | C07C 2/58 | (2006.01) |
| | C07C 2/60 | (2006.01) |
| | C07C 2/62 | (2006.01) |
| | C07C 2/64 | (2006.01) |
| | C07C 2/66 | (2006.01) |
| | C07C 2/70 | (2006.01) |
| | C07C 4/06 | (2006.01) |
| | B01J 19/24 | (2006.01) |
| | B01J 19/26 | (2006.01) |
| | C10G 29/20 | (2006.01) |
| | B01F 5/04 | (2006.01) |
| | C07C 5/27 | (2006.01) |
| | B01F 5/06 | (2006.01) |
| | C07C 4/00 | (2006.01) |
| | C07C 4/02 | (2006.01) |
| | C07C 5/22 | (2006.01) |
| | B01J 19/00 | (2006.01) |
| | C10G 29/00 | (2006.01) |
| | B01F 15/02 | (2006.01) |

(56) References Cited

U.S. PATENT DOCUMENTS

| | | | |
|---|---|---|---|
| 3,696,168 A | | 10/1972 | Vanderveen |
| 3,758,613 A | | 9/1973 | Anderson |
| 3,847,375 A | | 11/1974 | Kuerten et al. |
| 3,867,103 A | | 2/1975 | Boney et al. |
| 4,807,814 A | * | 2/1989 | Douche ............ B05B 7/1486 239/428 |
| 5,811,626 A | | 9/1998 | Joly et al. |
| 7,182,282 B2 | * | 2/2007 | Bedetti ............ B01J 2/16 239/424 |
| 7,956,230 B2 | | 6/2011 | Timken et al. |
| 8,183,425 B2 | | 5/2012 | Luo et al. |
| 8,198,499 B2 | | 6/2012 | Luo et al. |
| 8,569,561 B2 | | 10/2013 | Liu et al. |
| 8,692,048 B2 | | 4/2014 | Liu et al. |
| 2009/0166257 A1 | | 7/2009 | Luo |
| 2009/0171133 A1 | | 7/2009 | Luo |
| 2011/0282114 A1 | | 11/2011 | Luo et al. |
| 2012/0238779 A1 | | 9/2012 | Waters et al. |
| 2013/0004378 A1 | | 1/2013 | Luo et al. |
| 2013/0066130 A1 | | 3/2013 | Luo |

\* cited by examiner

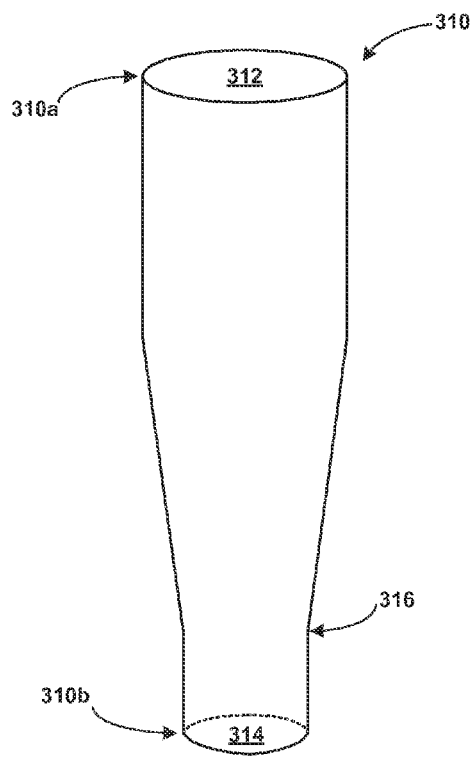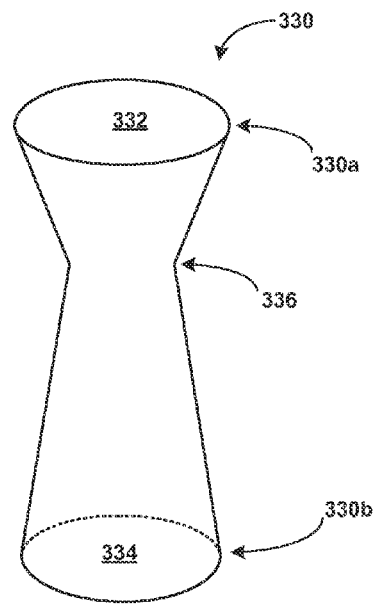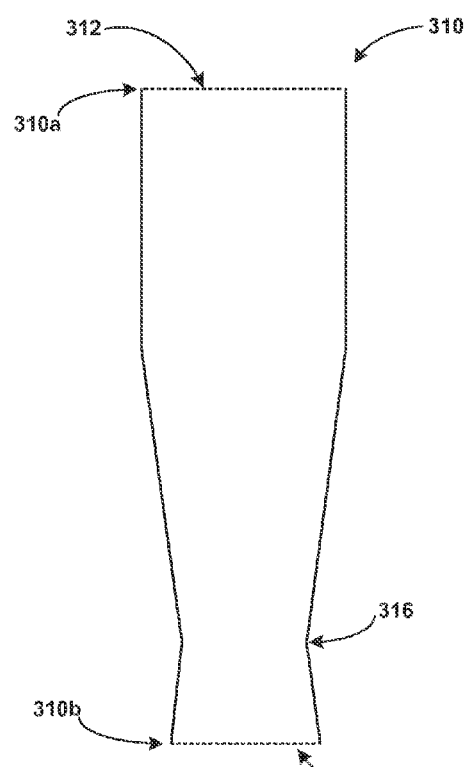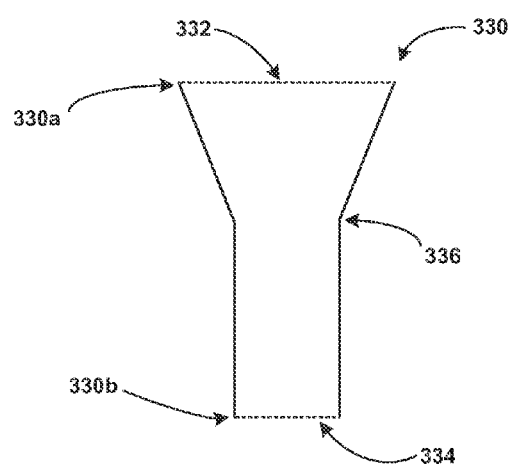
FIG. 3A
FIG. 4A
FIG. 4C
FIG. 3C

NOZZLE DESIGN FOR IONIC LIQUID CATALYZED ALKYLATION

TECHNICAL FIELD

This disclosure relates to apparatus, systems, and processes for ionic liquid catalyzed alkylation.

BACKGROUND

There is a need for apparatus and systems for the efficient mixing of two or more immiscible liquids, such as ionic liquid catalysts and hydrocarbon feeds for ionic liquid catalyzed hydrocarbon conversion processes including ionic liquid catalyzed alkylation.

SUMMARY

In an embodiment there is provided a system for ionic liquid catalyzed hydrocarbon conversion, the system comprising a reactor vessel having a top, and a mixing device disposed at the top of the reactor vessel. The mixing device comprises an upper venturi having an axial outlet at the upper venturi distal end, the upper venturi distal end disposed within the reactor vessel. The mixing device further comprises at least one feed injection array disposed within the reactor vessel, wherein each feed injection array comprises a plurality of feed injection nozzles. Each feed injection array is coaxial with the upper venturi. The mixing device still further comprises a lower venturi having an axial inlet at the lower venturi proximal end, wherein the lower venturi proximal end is disposed within the reactor vessel, and the lower venturi is coaxial with the upper venturi. The mixing device is configured for projecting a central jet of a first liquid downward from the upper venturi outlet into the lower venturi, and each feed injection array is configured for projecting a plurality of laterals jet of a second liquid toward the axis of the upper venturi.

In another embodiment, there is provided a system for ionic liquid catalyzed hydrocarbon conversion, the system comprising a reactor vessel having a top, a mixing device disposed at the top of the reactor vessel, and a circulation loop in fluid communication with the reactor vessel. The mixing device comprises an upper venturi having an axial outlet at the upper venturi distal end. The upper venturi distal end is disposed within the reactor vessel. The mixing device is configured for projecting a central jet of a first liquid downward from the upper venturi outlet. The mixing device further comprises at least one feed injection array disposed within the reactor vessel. Each feed injection array comprises a plurality of feed injection nozzles. Each feed injection array is configured for projecting a plurality of lateral jets of a second liquid toward the axis of the upper venturi. The mixing device still further comprises a lower venturi having an axial inlet at the lower venturi proximal end, the lower venturi being coaxial with the upper venturi. The lower venturi inlet is spaced radially outward from the upper venturi outlet to provide an inter-venturi channel between the lower venturi and the upper venturi. The circulation loop comprises a heat exchanger in fluid communication with the reactor vessel, wherein the heat exchanger is configured for cooling the reactor effluent of the reactor vessel. The circulation loop is in fluid communication with the mixing device for delivering cooled reactor effluent to the mixing device, wherein the first liquid comprises the cooled reactor effluent.

In yet another embodiment, there is provided a system for ionic liquid catalyzed hydrocarbon conversion, the system comprising a reactor vessel having a top and a vessel outlet; a mixing device in fluid communication with the reactor vessel, wherein the mixing device is disposed at the top of the reactor vessel; and a circulation loop in fluid communication with the vessel outlet. The system is configured for withdrawing reactor effluent from the reactor vessel via the vessel outlet into the circulation loop. The circulation loop comprises a heat exchanger configured for cooling withdrawn reactor effluent. The circulation loop is configured for recirculating at least a portion of the withdrawn reactor effluent to the mixing device to provide an external recirculation stream to the reactor vessel, wherein the external recirculation stream comprises the withdrawn reactor effluent. The mixing device comprises an upper venturi having an axial upper venturi inlet at the upper venturi proximal end and an axial upper venturi outlet at the upper venturi distal end. The upper venturi is in fluid communication with the circulation loop for receiving the external recirculation stream at the upper venturi inlet. The upper venturi is configured for projecting a central jet of the external recirculation stream axially downward from the upper venturi outlet, wherein the upper venturi outlet is disposed within the reactor vessel. The mixing device further comprises at least one feed injection array. Each feed injection array comprises a plurality of feed injection nozzles, wherein the axis of each feed injection nozzle intersects the axis of the upper venturi. Each feed injection array is configured for simultaneously projecting a plurality of lateral jets of hydrocarbon feed toward the central jet of the external recirculation stream. The mixing device still further comprises a lower venturi disposed coaxially with the feed injection array and with the upper venturi, the lower venturi having an axial lower venturi inlet at the lower venturi proximal end. The lower venturi inlet is spaced radially outward from the upper venturi outlet to define an inter-venturi channel between the upper venturi distal end and the lower venturi proximal end.

In still a further embodiment, there is provided a system for ionic liquid catalyzed hydrocarbon conversion comprising a reactor vessel having a top, and a mixing device disposed at the top of the reactor vessel. The mixing device comprises an upper venturi having an axial outlet at the upper venturi distal end, the upper venturi distal end disposed within the reactor vessel; a feed injection annulus disposed within the reactor vessel, the feed injection annulus having at least one feed injection port; and a lower venturi having an axial inlet at the lower venturi proximal end, the lower venturi proximal end disposed within the reactor vessel. The lower venturi is coaxial with the upper venturi. The mixing device is configured for projecting a central jet of a first liquid downward from the upper venturi outlet into the lower venturi. The feed injection annulus is configured for projecting a second liquid from each feed injection port toward the axis of the upper venturi.

In yet a further embodiment, there is provided a process for ionic liquid catalyzed hydrocarbon conversion, the process comprising withdrawing reactor effluent from a reactor vessel, the reactor effluent comprising unreacted hydrocarbons from a hydrocarbon feed; adding ionic liquid catalyst to the reactor effluent to provide an external recirculation stream; introducing the external recirculation stream into a mixing device, the mixing device in fluid communication with the reactor vessel, wherein the mixing device comprises an upper venturi having an axial outlet at the upper venturi distal end and a lower venturi having an axial inlet at the lower venturi proximal end; projecting a central jet of the external recirculation stream downward from the upper venturi outlet into the lower venturi; and, concurrently with the projecting of the central jet, projecting a hydrocarbon feed toward the central jet such that the hydrocarbon feed collides with the central jet, wherein the upper venturi distal end and the lower venturi proximal end are disposed within the reactor vessel, and the lower venturi is coaxial with the upper venturi.

Further embodiments of systems and processes for ionic liquid catalyzed hydrocarbon conversion are described herein below and shown in the Drawings. As used herein, the terms "comprising" and "comprises" mean the inclusion of named elements or steps that are identified following those terms, but not necessarily excluding other unnamed elements or steps.

BRIEF DESCRIPTION OF THE DRAWINGS

FIG. 3A schematically represents an upper venturi for a mixing device in perspective view, according to an embodiment of the present invention;

FIG. 3C schematically represents an upper venturi in sectional view, according to another embodiment of the present invention;

FIG. 4A schematically represents a lower venturi for a mixing device in perspective view, according to an embodiment of the present invention;

FIG. 4C schematically represents a lower venturi in sectional view, according to another embodiment of the present invention;

DETAILED DESCRIPTION

Figure 1A:
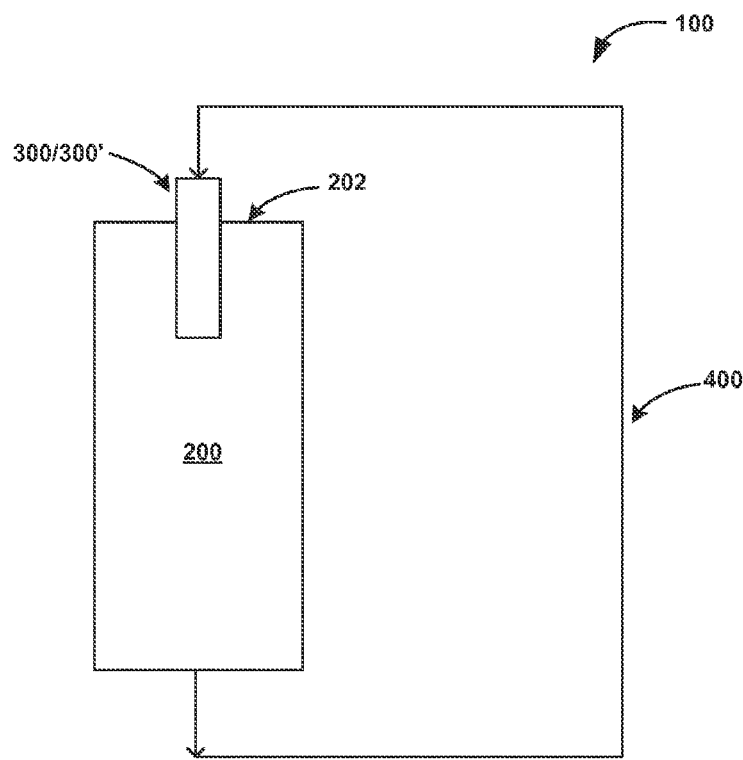
FIGS. 1A-1D each schematically represents a system for ionic liquid catalyzed hydrocarbon conversion, according to embodiments of the present invention.

Ionic liquid catalysts may be useful for a range of hydrocarbon conversion reactions, including alkylation reactions for the production of alkylate, e.g., comprising gasoline blending components, and the like. Systems for ionic liquid catalyzed hydrocarbon conversion according to this disclosure may comprise a reactor vessel, at least one mixing device per reactor vessel, and at least one circulation loop per reactor vessel. Each circulation loop may be in fluid communication with the reactor vessel and at least one mixing device. Each mixing device may comprise an upper venturi, at least one feed injection component, and a lower venturi. In an embodiment, the at least one feed injection component may comprise a feed injection array comprising a plurality of feed injection nozzles. In another embodiment, the at least one feed injection component may comprise a feed injection annulus.

Mixing devices as disclosed herein provide for the rapid and thorough mixing of ionic liquid catalyst and hydrocarbon reactants so as to generate a large surface area of ionic liquid catalyst phase in an ionic liquid/hydrocarbon mixture, thereby enabling highly efficient ionic liquid catalyzed hydrocarbon conversion processes on a commercial scale.

Systems for Ionic Liquid Catalyzed Alkylation

Although systems may be described herein primarily with reference to ionic liquid catalyzed alkylation reactions, such systems may also be applicable to other ionic liquid catalyzed hydrocarbon conversion reactions as well as to other processes more generally.

In an embodiment, a system for ionic liquid catalyzed hydrocarbon conversion may comprise a reactor vessel and a mixing device disposed at the top of the reactor vessel. The top of the reactor vessel may also be referred to herein as the reactor vessel top. The mixing device may be disposed vertically at the reactor vessel top and the mixing device may extend distally from the reactor vessel top into the reactor vessel. The mixing device may also extend proximally above the reactor vessel top.

In an embodiment, each mixing device may comprise an upper venturi, a plurality of feed injection nozzles, and a lower venturi. In an embodiment, the lower venturi may be disposed below, i.e., generally at a lower elevation than, the upper venturi. In an embodiment, the upper venturi proximal end may be disposed above the reactor vessel top such that the upper venturi proximal end is located outside the reactor vessel, while the upper venturi distal end and the entire lower venturi may be disposed below the reactor vessel top and within the reactor vessel.

The upper venturi may have an axial inlet at the upper venturi proximal end and an axial outlet at the upper venturi distal end. The outlet of the upper venturi may be referred to herein as the upper venturi outlet. The upper venturi distal end may be disposed within the reactor vessel. In an embodiment, the upper venturi may have a constriction point at an elevation above the upper venturi outlet and below the upper venturi inlet. The mixing device may be configured for projecting a central jet of a first liquid downward from the upper venturi outlet into the lower venturi. In an embodiment, the central jet may be projected downward at high speed from the upper venturi outlet into the lower venturi to form a local lower pressure region in the lower venturi due to the Venturi effect. This lower pressure region may draw liquid from the vicinity of the feed injection nozzles into the lower venturi resulting in rapid mixing and mass transfer among liquid streams in the lower venturi. The central jet of the first liquid may be coaxial with the upper venturi.

In an embodiment, the mixing device may be configured for projecting the central jet from the upper venturi on a continuous or uninterrupted basis over an extended time period, e.g., between shut-down operations of a reactor or system for service or maintenance. In an embodiment, the first liquid (e.g., central jet) may comprise an external recirculation stream of the reactor vessel. In an embodiment, the external recirculation stream may comprise reactor effluent from the reactor vessel in combination with fresh ionic liquid catalyst, wherein the reactor effluent may comprise unreacted hydrocarbons from a hydrocarbon feed. In an embodiment, the central jet may consist essentially or entirely of liquid(s), e.g., the first liquid may be at least substantially free of gas(es) and gaseous phase materials.

The plurality of feed injection nozzles of the mixing device may be configured or assembled into at least one feed injection array, such that each feed injection array comprises a plurality of the feed injection nozzles. Each feed injection array may be disposed within the reactor vessel. Each feed injection array may be configured for projecting a plurality of lateral jets of a second liquid toward the axis of the upper venturi. In an embodiment, each feed injection nozzle may be configured for projecting one of the lateral jets toward the central jet. In an embodiment, each feed injection nozzle may be configured for projecting one of the lateral jets at high speed such that each lateral jet impinges on the central jet with sufficient momentum to create highly turbulent flow within the mixing device for optimal mixing between the first and second liquid streams. In an embodiment, each mixing device may be configured for projecting the lateral jets on a continuous or uninterrupted basis over an extended time period, e.g., between shut-down operations of the reactor or system for service or maintenance. In an embodiment, the second liquid may comprise a hydrocarbon feed, and the system may be configured for ionic liquid catalyzed alkylation.

In an embodiment, the mixing device may be configured such that the axis of each of the plurality of feed injection nozzles is at an angle in the range from 0° to 90° to the axis of the upper venturi. In a sub-embodiment, the axis of each of the plurality of feed injection nozzles may intersect the axis of the upper venturi at an angle, θ (see, e.g., FIG. 5A), wherein θ is greater than (>) 0° and not greater than (≤) 90°. In another sub-embodiment, the axis of each of the plurality of feed injection nozzles may intersect the axis of the upper venturi at an angle, θ, in the range from 20° to 90°, or from 25° to 90°, or from 30° to 90°.

In a further sub-embodiment, the axis of each of the plurality of feed injection nozzles may intersect the axis of the upper venturi at an angle, θ, in the range from 80° to 90°, or from 85° to 90°, or at substantially a right angle. In an embodiment, the axis of each of the plurality of feed injection nozzles may intersect the axis of the upper venturi at an elevation below (distal to) the upper venturi outlet. In an embodiment, the axis of each of the plurality of feed injection nozzles of a given feed injection array may intersect the axis of the upper venturi at a common intersection.

The lower venturi may have an axial inlet at the lower venturi proximal end, wherein the lower venturi proximal end is disposed within the reactor vessel. The inlet of the lower venturi may be referred to herein as the lower venturi inlet. The lower venturi may extend distally of the plurality of feed injection nozzles. In an embodiment, each feed injection array and the lower venturi may be disposed coaxially with the upper venturi.

In an embodiment, the plurality of feed injection nozzles of a given feed injection array may be symmetrically arranged therein. In an embodiment, the feed injection nozzles may be symmetrically arranged in each feed injection array, and the feed injection nozzles may be evenly spaced, or unevenly spaced, in the feed injection array. In an embodiment, the ratio of a first liquid linear velocity of the central jet from the upper venturi outlet to a second liquid linear velocity of the lateral jets from the feed injection nozzles may be in the range from 0.1-10, or from 0.2-5, or from 0.8-1.2. In a sub-embodiment, the system may be configured such that a first liquid linear velocity of the central jet from the upper venturi outlet is at least substantially equal to a second liquid linear velocity of each lateral jet from the feed injection nozzles.

In an embodiment, each feed injection array may comprise from six (6) to 50 of the feed injection nozzles, or from eight (8) to 40 of the feed injection nozzles, or from 10 to 30 of the feed injection nozzles. In an embodiment, the plurality of feed injection nozzles of a given feed injection array may be arranged annularly, e.g., in the form of a ring of the feed injection nozzles per feed injection array. In an embodiment, each lateral jet may be coaxial with the axis of its respective feed injection nozzle. In an embodiment, the axis of each lateral jet may intersect the axis of the central jet at an elevation below the upper venturi outlet. In an embodiment, the axes of all the lateral jets of a given feed injection array may intersect the axis of the central jet at a common intersection.

In an embodiment, a feed injection array may be disposed at the same elevation or about the same elevation as the lower venturi inlet. In a sub-embodiment, the upper venturi outlet may be at the same elevation or about the same elevation as the lower venturi inlet. A feed injection array disposed at, or near, the upper venturi outlet or the lower venturi inlet may allow for rapid or instant mixing between the first liquid and the second liquid within the lower venturi. By the term "elevation" is meant the height at which an element, structure, feature, or component is disposed, e.g., relative to the height of another element, structure, feature, or component.

In another embodiment, the lower venturi has a constriction point and a feed injection array may be disposed at the same elevation or about the same elevation as the lower venturi constriction point. The lower venturi constriction point may be at an elevation below the lower venturi inlet and above the lower venturi outlet. In a sub-embodiment, the feed injection nozzles of a feed injection array may be disposed within the lower venturi.

In an embodiment, the at least one feed injection array of a given mixing device may comprise a single feed injection array, wherein the single feed injection array may be disposed at a first elevation of the mixing device or at a second elevation of the mixing device. The first elevation may be at the same elevation or about the same elevation as the lower venturi inlet, and the second elevation may be at the same elevation or about the same elevation as the lower venturi constriction point.

In another embodiment, the at least one feed injection array of a given mixing device may comprise a first feed injection array disposed at a first elevation of the mixing device and a second feed injection array disposed at a second elevation of the mixing device, wherein the first elevation may be at the same elevation or about the same elevation as the lower venturi inlet and the second elevation may be at the same elevation or about the same elevation as the lower venturi constriction point. Liquid flow at, or near, both the first elevation and the second elevation may be highly turbulent.

In the context of describing the elevation of a feed injection array relative to the lower venturi, the expression "the same elevation or about the same elevation" means that a feed injection array may be disposed at an elevation within a range spanning a maximum distance above or below a given reference point of the lower venturi as defined hereinbelow. For a feed injection array disposed at a first elevation that is at the same elevation or about the same elevation as the lower venturi inlet, the lower venturi proximal end may be used as the reference point, and the feed injection array may be disposed at an elevation within a range spanning a distance not greater than ($\leq$) $0.5E_{A1}$ above or below the lower venturi proximal end, wherein the distance $E_{A1}$ equals 20% of the diameter, $D_{UO}$, of the upper venturi outlet ($E_{A1}=0.2D_{UO}$). (See, for example, FIG. 4B.) For a feed injection array disposed at a second elevation that is at the same elevation or about the same elevation as the lower venturi constriction point, the lower venturi constriction point may be used as the reference point, and the feed injection array may be disposed at an elevation within a range spanning a distance not greater than ($\leq$) $0.5E_{A2}$ above or below the lower venturi constriction point, wherein the distance $E_{A2}$ equals 20% of the internal diameter, $D_{LC}$, of the lower venturi constriction point ($E_{A2}=0.2D_{LC}$). (See, for example, FIG. 4B.) One of ordinary skill will recognize that the distances $E_{A1}$ and $E_{A2}$ are being used herein for relative measurement only and accordingly have arbitrary units. Other elevations for the feed injection array(s) relative to the lower venturi are also possible. In an embodiment, the elevation of the feed injection array(s) may be selected: 1) to increase or maximize the volume of the internal recirculation stream drawn into the mixing device by a lower pressure region formed within the lower venturi due to the Venturi effect, and/or 2) to increase or maximize the turbulence and the mixing intensity of fluid streams within the lower venturi.

In an embodiment, each feed injection nozzle of the mixing device may project one of the lateral jets toward the upper venturi axis. In an embodiment, each of the feed injection nozzles may terminate in a nozzle outlet (see, for example, FIGS. 11A-11B). In an embodiment wherein the feed injection array may be disposed at the same elevation or about the same elevation as the lower venturi proximal end, each of the feed injection nozzles may terminate at the same radial location or about the same radial location as the perimeter of the upper venturi outlet. In the context of describing the radial location of each nozzle terminus relative to the perimeter of the upper venturi outlet, the expression "the same radial location or about the same radial location" means that the terminus of each feed injection nozzle may be disposed within a radial distance not greater than ($\leq$) $0.2D_{UO}$ radially inward or radially outward from the perimeter of the upper venturi outlet, wherein $D_{UO}$ is the diameter of the upper venturi outlet. Other radial locations for the feed injection nozzles relative to the perimeter of the upper venturi outlet are also possible. In an embodiment, the radial location of the feed injection nozzles may be selected to decrease or minimize the mixing time between the liquid flow from the feed injection nozzles and the flow from the upper venturi outlet.

In an embodiment wherein the feed injection array may be disposed at the same elevation or about the same elevation as the lower venturi constriction point, the terminus of each feed injection nozzle may be disposed at a radial distance in the range from 0.2 to $0.5D_{LC}$ radially outward from the lower venturi axis, $A_L$, or in the range from $0.4D_{LC}$ to $0.5D_{LC}$, radially outward from the lower venturi axis, $A_L$; wherein $D_{LC}$ is the internal diameter of the lower venturi constriction point.

In an embodiment, the lower venturi may have an axial inlet at the lower venturi proximal end, such that the lower venturi inlet is at the same elevation as the lower venturi proximal end. In this context, the term "axial inlet" means that the lower venturi inlet coincides with, or occupies the same space as, the axis of the lower venturi. Similarly, in an embodiment the upper venturi may have an axial outlet at the upper venturi distal end, such that the upper venturi outlet is at the same elevation as the upper venturi distal end. In this context, the term "axial outlet" means that the upper venturi outlet coincides with, or occupies the same space as, the axis of the upper venturi.

In an embodiment, the lower venturi proximal end may be disposed at the same elevation or about the same elevation as the upper venturi distal end. In the context of describing the elevation of the lower venturi proximal end relative to the upper venturi distal end, the expression "the same elevation or about the same elevation" means that the lower venturi proximal end may be disposed at an elevation within a range spanning a distance not greater than ($\leq$) $0.5E_L$ above or below the upper venturi distal end, wherein the distance $E_L$ equals 20% of the diameter, $D_{LI}$, of the lower venturi inlet ($E_L=0.2D_{LI}$) (see, for example, FIG. 3B). One of ordinary skill will recognize that the distance $E_L$ is being used herein for relative measurement only and accordingly has arbitrary units. Other elevations for the lower venturi proximal end relative to the upper venturi distal end are also possible.

In an embodiment, the lower venturi proximal end may be spaced radially outward from the upper venturi distal end to provide an inter-venturi channel; or, stated differently: the lower venturi inlet may be spaced radially outward from the upper venturi outlet to provide the inter-venturi channel. In an embodiment, the inter-venturi channel may be configured to allow liquid(s) to be drawn therethrough into the lower venturi, for example, via the Venturi effect. In an embodiment, each of the upper venturi outlet and the lower venturi inlet may be circular, and the inter-venturi channel may comprise an annular or substantially annular channel.

In an embodiment, the system may further comprise a circulation loop in fluid communication with the reactor vessel and the mixing device. The circulation loop may have a first loop end coupled to a vessel outlet of the reactor vessel for withdrawing reactor effluent from the reactor vessel into the circulation loop. The circulation loop may further have a second loop end coupled to the mixing device for introducing the first liquid into the reactor vessel via the mixing device. In an embodiment, the circulation loop may comprise a loop outlet, an ionic liquid catalyst inlet, a circulation pump, a heat exchanger, and at least one circulation loop conduit (see, for example, FIG. 1D).

In an embodiment, the loop outlet may be configured for removing a portion of the withdrawn reactor effluent from the circulation loop. In an embodiment, the ionic liquid catalyst inlet may be configured for adding fresh ionic liquid catalyst to the withdrawn reactor effluent within the circulation loop to provide the first liquid, i.e., the first liquid may comprise the withdrawn reactor effluent in combination with the fresh ionic liquid catalyst. In an embodiment, the first liquid may be delivered, via the circulation loop and the mixing device, to the top of the reactor vessel to provide an external recirculation stream.

In an embodiment, the heat exchanger may be configured for cooling the first liquid within the circulation loop. In an embodiment, the least one circulation loop conduit may be coupled to, and in fluid communication with, each of the vessel outlet, the circulation pump, the heat exchanger, and the mixing device. In an embodiment, the circulation pump may be configured for pumping the first liquid through the circulation loop, e.g., to the heat exchanger and the mixing device.

In an embodiment, the system may comprise a plurality of the circulation loops per reactor vessel, wherein each circulation loop may be in fluid communication with the reactor vessel and at least one mixing device. In an embodiment, the system may further comprise a static mixer in fluid communication with the heat exchanger and the mixing device. In an embodiment, the static mixer may be disposed downstream from the heat exchanger and upstream from the mixing device.

In a further embodiment of a system for ionic liquid catalyzed hydrocarbon conversion, the system may comprise a reactor vessel having a top, at least one mixing device, and at least one circulation loop. Each mixing device may be disposed at the top of the reactor vessel. Each circulation loop may be in fluid communication with the reactor vessel. Each mixing device may comprise an upper venturi, at least one feed injection array, and a lower venturi. The upper venturi may have an axial outlet at the upper venturi distal end, and the upper venturi may be disposed vertically at the top of the reactor vessel such that the upper venturi outlet is inside the reactor vessel.

The system may be configured for projecting a central jet of a first liquid downward from the upper venturi outlet. The lower venturi may have an axial inlet at the lower venturi proximal end, and the central jet of the first liquid may be projected downward in an axial direction from the upper venturi outlet into the lower venturi inlet. Each feed injection array may comprise a plurality of feed injection nozzles. Each feed injection array may be disposed within the reactor vessel. Each feed injection array may be configured for projecting a plurality of lateral jets of a second liquid toward the upper venturi axis, wherein the central jet of the first liquid may be coaxial with the upper venturi.

The lower venturi may be disposed coaxially with the upper venturi. The lower venturi inlet may be spaced radially outward from the upper venturi outlet to provide or define an inter-venturi channel between the lower venturi and the upper venturi. In an embodiment, the lower venturi proximal end may be disposed at the same elevation or about the same elevation as the upper venturi distal end. In another embodiment, the lower venturi proximal end may be disposed at an elevation below the upper venturi distal end. In a further embodiment, the lower venturi proximal end may be disposed at an elevation above the upper venturi distal end, and in a sub-embodiment the lower venturi proximal end may be disposed at an elevation between the upper venturi constriction point and the upper venturi distal end.

Each circulation loop may comprise a heat exchanger, in fluid communication with the reactor vessel, for cooling reactor effluent from the reactor vessel to provide cooled reactor effluent. The circulation loop may be in fluid communication with the mixing device for delivering the cooled reactor effluent thereto. In an embodiment, the first liquid (e.g., central jet) projected from the upper venturi outlet may comprise the cooled reactor effluent in combination with fresh ionic liquid catalyst. The central jet of the first liquid may be projected into the reactor vessel via the mixing device.

According to yet another embodiment of a system for ionic liquid catalyzed hydrocarbon conversion, the system may comprise a reactor vessel having a top and a vessel outlet, at least one mixing device in fluid communication with the reactor vessel, and a circulation loop in fluid communication with the vessel outlet and the mixing device. Each mixing device may be disposed at the top of the reactor vessel.

The circulation loop may be in fluid communication with the vessel outlet. The system may be configured for withdrawing reactor effluent from the reactor vessel via the vessel outlet into the circulation loop. The circulation loop may comprise a heat exchanger configured for cooling withdrawn reactor effluent. The circulation loop may be configured for recirculating at least a portion of the withdrawn reactor effluent to the mixing device to provide an external recirculation stream to the reactor vessel, wherein the external recirculation stream may comprise the withdrawn reactor effluent. The reactor vessel may also have an internal recirculation stream.

The expression "internal recirculation stream" may be used herein to refer to a stream of liquid within the reactor vessel that flows through and around the mixing device. In an embodiment, the internal recirculation stream may flow downward through the inter-venturi channel into the lower venturi, downward through the interior of the lower venturi, and out of the lower venturi outlet. The flow rate of the internal recirculation stream may be quantified as the volume of liquid flowing through the inter-venturi channel per unit time. The flow rate of the external recirculation stream may be quantified as the volume of liquid flowing from the upper venturi outlet per unit time. The ratio of the flow rate of the internal recirculation stream to the flow rate of the external recirculation stream may typically be in the range from 0.1 to 10, or from 0.2 to 5, or from 0.25 to 4.

In an embodiment, apart from the mixing device(s) and any reactor monitoring instrumentation and the like, the reactor vessel may be entirely filled with liquid (e.g., comprising ionic liquid catalyst, reactants, and alkylate product). The internal recirculation stream of the reactor vessel may serve, inter alia, to dilute the hydrocarbon feed in the mixing device and to decrease the local olefin concentration so as to provide superior product(s), e.g., alkylate. In an embodiment, the flow of the internal recirculation stream within the reactor vessel may be driven solely by the flow of liquid(s), including the external recirculation stream, through the mixing device.

Each mixing device may comprise an upper venturi having an axial upper venturi inlet and an axial upper venturi outlet, at least one feed injection array, and a lower venturi disposed coaxially with each feed injection array and the upper venturi. The upper venturi may be in fluid communication with the circulation loop for receiving the external recirculation stream, e.g., at the upper venturi inlet. The upper venturi may be configured for projecting a central jet of the external recirculation stream ($1^{st}$ liquid) axially downward from the upper venturi outlet, wherein the upper venturi outlet is disposed within the reactor vessel.

Each feed injection array may comprise a plurality of feed injection nozzles. In an embodiment, the axis of each feed injection nozzle intersects the axis of the upper venturi (see, for example, FIG. 5A). Each feed injection array may be configured for simultaneously projecting a plurality of lateral jets of hydrocarbon feed (second liquid) toward the central jet of the external recirculation stream. That is to say, the system may be configured to project a plurality of lateral jets from the feed injection array concurrently with projection of the central jet from the upper venturi outlet. In an embodiment, the system may be configured such that the lateral jets of hydrocarbon feed collide with the central jet of the external recirculation stream. Stated differently, the system may be configured such that the central jet collides with each of the lateral jets. The system may be further configured for projecting both the central jet and the plurality of lateral jets for extended time periods, e.g. continuously during the entire time that the system is operating.

The lower venturi may comprise a lower venturi proximal end having an axial lower venturi inlet. In an embodiment, the lower venturi inlet may be disposed at the same elevation or about the same elevation as the upper venturi outlet. In an embodiment, the lower venturi inlet may be spaced radially outward from the upper venturi outlet to provide or define an inter-venturi channel between the upper venturi distal end and the lower venturi proximal end. In an embodiment, each of the lower venturi inlet and the upper venturi outlet may be at least substantially circular, and the inter-venturi channel may be at least substantially annular. In an embodiment, the inter-venturi channel may be configured for circulation therethrough of the internal recirculation stream of the reactor vessel (see, for example, FIGS. 6A-6B).

According to still a further embodiment of a system for ionic liquid catalyzed hydrocarbon conversion, the system may comprise a reactor vessel and a mixing device. The mixing device may be disposed, e.g., vertically, at the reactor vessel top, the mixing device may extend distally from the reactor vessel top into the reactor vessel, and the mixing device may also extend proximally above the reactor vessel top.

In an embodiment, each mixing device may comprise an upper venturi, a feed injection annulus, and a lower venturi. In an embodiment, the lower venturi may be disposed below, i.e., generally at a lower elevation than, the upper venturi. In an embodiment, the upper venturi distal end, the feed injection annulus, and the entire lower venturi may be disposed below the reactor vessel top and within the reactor vessel.

The upper venturi may have an axial inlet at the upper venturi proximal end and an axial outlet at the upper venturi distal end. The upper venturi distal end may be disposed within the reactor vessel. The upper venturi, the lower venturi, and the reactor vessel may be juxtaposed and configured generally as described hereinabove with reference to other embodiments of a system for ionic liquid catalyzed hydrocarbon conversion and/or as described with reference to FIG. 12A, infra. The mixing device may be configured for projecting a central jet of a first liquid downward from the upper venturi outlet into the lower venturi. The central jet of the first liquid may be coaxial with the upper venturi.

In an embodiment, the mixing device may be configured for projecting the central jet from the upper venturi on a continuous or uninterrupted basis, substantially as described hereinabove with reference to other embodiments. The first liquid (e.g., central jet) may comprise an external recirculation stream of the reactor vessel. In an embodiment, the external recirculation stream may comprise withdrawn reactor effluent in combination with fresh ionic liquid catalyst.

The lower venturi may have an axial inlet at the lower venturi proximal end, wherein the lower venturi proximal end is disposed within the reactor vessel. The inlet of the lower venturi may be referred to herein as the lower venturi inlet. The lower venturi may be disposed coaxially with the upper venturi. In an embodiment, the feed injection annulus may be disposed coaxially with the upper venturi and at the same elevation or about the same elevation as the lower venturi inlet, e.g., at, or near, the upper venturi outlet. In the context of describing the elevation of a feed injection annulus relative to the lower venturi, the expression "the same elevation or about the same elevation" has the same meaning as defined herein with respect to the elevation of a feed injection array relative to the lower venturi (see, e.g., FIGS. 12A and 4B).

The feed injection annulus may have at least one feed injection port. The feed injection annulus may be configured for projecting a second liquid from each feed injection port toward the axis of the upper venturi. In an embodiment, the second liquid may be projected from each feed injection port as a jet of the second liquid. In an embodiment, the system may be configured such that at least one jet of the second liquid collides with the central jet of the first liquid from the upper venturi outlet. Each mixing device may be configured for projecting the second liquid on a continuous or uninterrupted basis, substantially as described hereinabove with respect to other embodiments of a system for ionic liquid catalyzed hydrocarbon conversion. In an embodiment, the second liquid may comprise a hydrocarbon feed, and the system may be configured for ionic liquid catalyzed alkylation.

In an embodiment, the feed injection annulus may have a single feed injection port. In a sub-embodiment, a single feed injection port of the feed injection annulus may be in the form of an annular slit in an inner portion of the feed injection annulus (see, for example, FIGS. 12C-12D). In another embodiment, the feed injection annulus may have from two (2) to 50 feed injection ports, or from four (4) to 40 feed injection ports, or from six (6) to 30 feed injection ports.

In an embodiment, a plurality of the feed injection ports may be symmetrically arranged on an inner portion of the feed injection annulus. In an embodiment, the feed injection ports may be evenly spaced, or unevenly spaced, on the feed injection annulus. The feed injection ports may be of various shapes or configurations, including substantially circular, oval, and square. In another embodiment, the feed injection ports may be in the form of elongated arcuate slits. In a further embodiment, one or more feed injection ports may each be in the form of an annular slit. In yet another embodiment, a given feed injection annulus may have a combination of differently shaped feed injection ports. In general, the size (area), arrangement, and/or number of the feed injection ports of a given feed injection annulus may be selected as appropriate in relation to various process parameters, including the flow rate of the external- and internal recirculation streams through the mixing device. In an embodiment, the system may be configured such that a first liquid linear velocity of the central jet from the upper venturi outlet is at least substantially equal to a second liquid linear velocity of each jet of the second liquid projected from the feed injection annulus.

In an embodiment, each feed injection port of the feed injection annulus may be at the same radial location or about the same radial location as the perimeter of the upper venturi outlet. In the context of describing the radial location of each feed injection port relative to the perimeter of the upper venturi outlet, the expression "the same radial location or about the same radial location" means that each feed injection port may be disposed within a radial distance not greater than ($\leq$) $0.2D_{UO}$ radially inward or radially outward from the perimeter of the upper venturi outlet, wherein $D_{UO}$ is the diameter of the upper venturi outlet. Other radial locations for the feed injection port(s) relative to the perimeter of the upper venturi outlet are also possible.

In an embodiment, the lower venturi inlet may be disposed at the same elevation or about the same elevation as the upper venturi outlet. In the context of describing the elevation of the lower venturi proximal end relative to the upper venturi distal end, the expression "the same elevation or about the same elevation" has the same meaning as defined herein with respect to other embodiments of a mixing device (see, e.g., FIG. 3B). Other elevations for the lower venturi inlet relative to the upper venturi outlet are also possible.

In an embodiment, the lower venturi inlet may be spaced radially outward from the upper venturi outlet to provide an inter-venturi channel. In an embodiment, the inter-venturi channel may be configured as described hereinabove. In an embodiment, each of the upper venturi outlet and the lower venturi inlet may be circular, and the inter-venturi channel may comprise an annular or substantially annular channel.

In an embodiment, the system may further comprise a circulation loop in fluid communication with the reactor vessel and the mixing device. The circulation loop may have a first loop end coupled to a vessel outlet of the reactor vessel for withdrawing reactor effluent from the reactor vessel into the circulation loop, and a second loop end coupled to the mixing device. The circulation loop may comprise an ionic liquid catalyst inlet configured for adding fresh ionic liquid catalyst to withdrawn reactor effluent, and a heat exchanger configured for cooling the first liquid (see, for example, FIG. 1D).

According to yet a further embodiment, a process for ionic liquid catalyzed hydrocarbon conversion, e.g., isoparaffin/olefin alkylation, may be practiced using systems as disclosed herein. Such systems may comprise a reactor vessel having a vessel outlet, at least one mixing device in fluid communication with the reactor vessel, and a circulation loop in fluid communication with the vessel outlet and the mixing device. The mixing device may comprise an upper venturi having an axial outlet at the upper venturi distal end, and a lower venturi having an axial inlet at the lower venturi proximal end. The upper venturi distal end and the lower venturi proximal end may be disposed within the reactor vessel, and the lower venturi may be coaxial with the upper venturi. The mixing device may further comprise at least one feed injection component disposed within the reactor vessel. In an embodiment, each mixing device may be disposed vertically in the top of the reactor vessel. Such systems may further comprise additional elements, features, and characteristics as described herein and as shown in the drawings.

Processes for ionic liquid catalyzed hydrocarbon conversion may include: withdrawing reactor effluent from the reactor vessel via the circulation loop, adding fresh ionic liquid catalyst to the withdrawn reactor effluent to provide an external recirculation stream, and introducing the external recirculation stream into the mixing device. A portion of the withdrawn reactor effluent may be removed from the circulation loop for fractionation to provide an alkylate product. In an embodiment, the reactor effluent or external recirculation stream may be cooled in the circulation loop prior to introducing the external recirculation stream into the mixing device.

In an embodiment, a process for ionic liquid catalyzed hydrocarbon conversion may further include: projecting a central jet of the external recirculation stream downward from the upper venturi outlet into the lower venturi inlet; and, concurrently with the projecting of the central jet, additionally projecting a hydrocarbon feed toward the central jet such that the hydrocarbon feed collides with the central jet. In an embodiment, the central jet may be coaxial with the axis of the upper venturi.

The central jet may comprise an ionic liquid/hydrocarbon emulsion comprising small to microscopic droplets of the ionic liquid catalyst, e.g., having an ionic liquid catalyst droplet diameter in the range from 1 to 1000 microns, or from 5 to 250 microns, or from 10 to 150 microns. In an embodiment, the hydrocarbon feed may collide with the central jet, such that the hydrocarbon feed contacts a large surface area of the ionic liquid catalyst. Such contacting of the hydrocarbon feed with the ionic liquid catalyst may be under alkylation conditions so as to provide alkylate product(s).

Processes for ionic liquid catalyzed hydrocarbon conversion may still further include circulating an internal recirculation stream of the reactor vessel through the lower venturi of the mixing device. Accordingly, both the external- and internal recirculation streams may flow through the lower venturi. In an embodiment, the ratio of the flow rate (vol. per unit time) of the internal recirculation stream to the flow rate of the external recirculation stream during processes as disclosed herein may typically be in the range from 0.1 to 10, or from 0.2 to 5, or from 0.25 to 4. In an embodiment, the lower venturi inlet may be spaced radially outward from the upper venturi outlet to provide an inter-venturi channel, and the internal recirculation stream may be circulated through the lower venturi via the inter-venturi channel.

In an embodiment, the at least one feed injection component of the mixing device may comprise a feed injection annulus having at least one feed injection port. In an embodiment of a process for ionic liquid catalyzed hydrocarbon conversion, the hydrocarbon feed may be projected toward the central jet via the at least one feed injection port of the feed injection annulus.

In another embodiment, the at least one feed injection component of the mixing device may comprise a feed injection array disposed within the reactor vessel, and the feed injection array may comprise a plurality of feed injection nozzles. In an embodiment of a process for ionic liquid catalyzed hydrocarbon conversion, the hydrocarbon feed may be projected toward the central jet, e.g., as a plurality of lateral jets, via the feed injection nozzles.

Figure 8A:
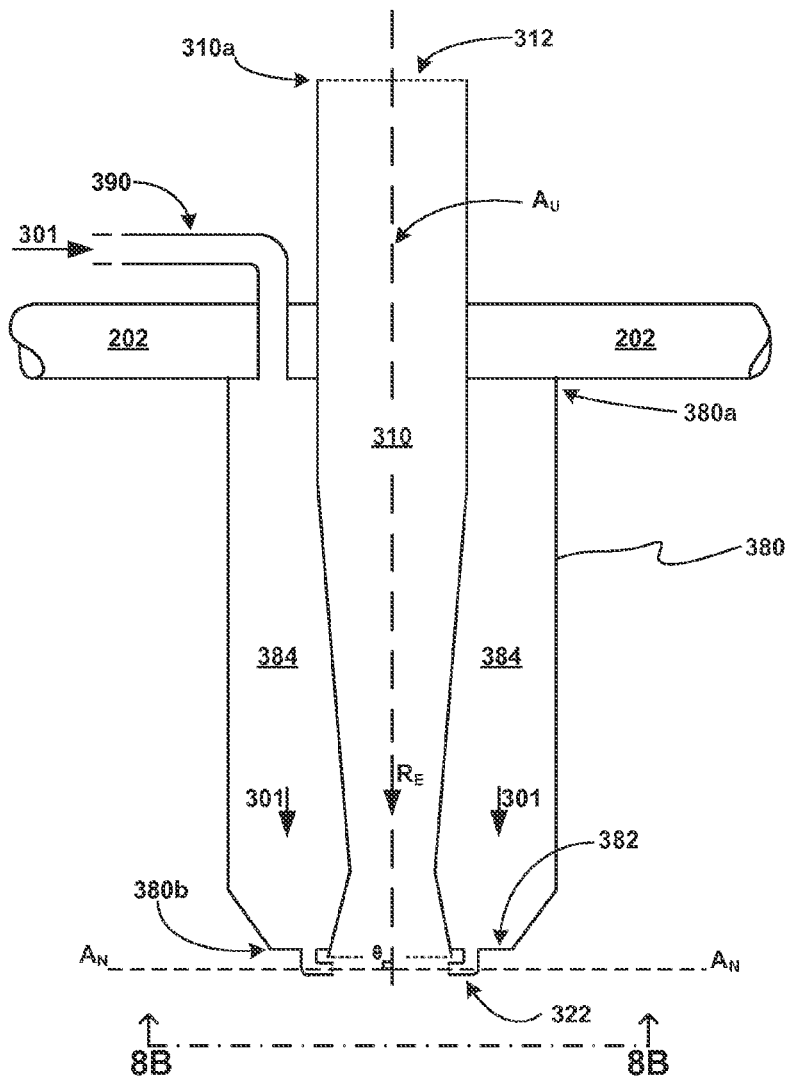
FIG. 8A schematically represents a portion of a mixing device, in sectional view.
Figure 8B:
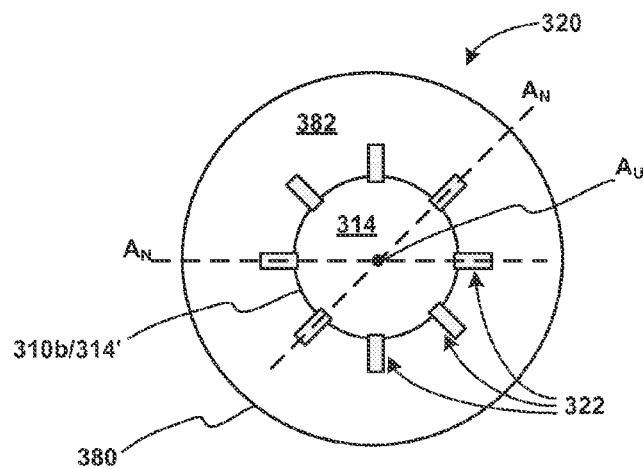
FIG. 8B shows a feed injection array of the mixing device, as seen along the line 8B-8B of FIG. 8A, according an embodiment of the present invention.

In an embodiment, a feed injection array of the mixing device may be disposed at the same elevation or about the same elevation as the lower venturi inlet, and the feed injection nozzles may terminate at a location radially inward from the perimeter of the upper venturi outlet such that the central jet may collide with at least a terminal portion of each feed injection nozzle (see, for example, FIGS. 8A-8B). In another embodiment, the feed injection array may be disposed at an elevation below the lower venturi inlet, and the feed injection nozzles may extend radially inward into the lower venturi such that at least one of the external recirculation stream and the internal recirculation stream may collide with at least a terminal portion of each feed injection nozzle (see, for example, FIG. 10).

In an embodiment, the hydrocarbon feed may be introduced directly into the lower venturi, e.g., via a plurality of feed injection nozzles disposed within the lower venturi. In a sub-embodiment, a plurality of the feed injection nozzles may be disposed within the lower venturi at the same elevation or about the same elevation as the lower venturi constriction point.

In an embodiment, the hydrocarbon feed may comprise at least one $C_2$-$C_{10}$ olefin and at least one $C_4$-$C_{10}$ isoparaffin. In an embodiment, the ionic liquid catalyst may comprise a chloroaluminate ionic liquid. In an embodiment, the alkylation conditions may comprise a temperature in the range from −40° C. to 150° C., and a pressure in the range from atmospheric pressure to 8000 kPa. In an embodiment, the overall ionic liquid catalyst volume in the reactor vessel may be maintained in the range from 0.5 to 50 vol %, or from 1 to 10 vol %, or from 2 to 6 vol %. Hydrocarbon feeds, ionic liquid catalysts, and conditions for ionic liquid catalyzed alkylation are described hereinbelow.

In an embodiment, a process for ionic liquid catalyzed hydrocarbon conversion may still further include feeding a portion of the reactor effluent from the circulation loop to an ionic liquid/hydrocarbon separator; via the ionic liquid/hydrocarbon separator, separating the portion of reactor effluent into an ionic liquid catalyst phase and a hydrocarbon phase; and via a fractionation unit, separating an alkylate product from the hydrocarbon phase.

Figure 1B:
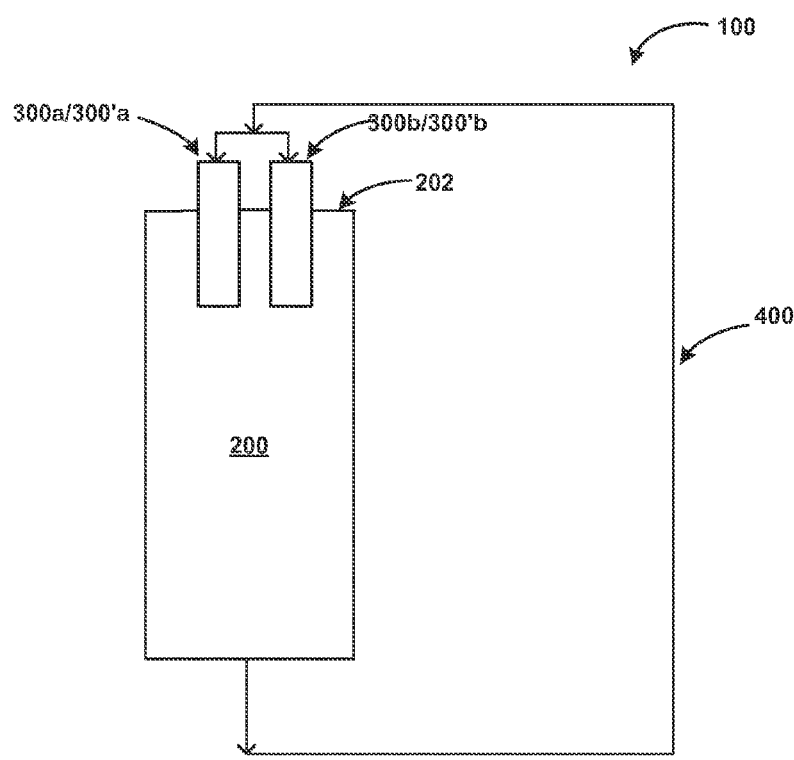
Figure 1C:
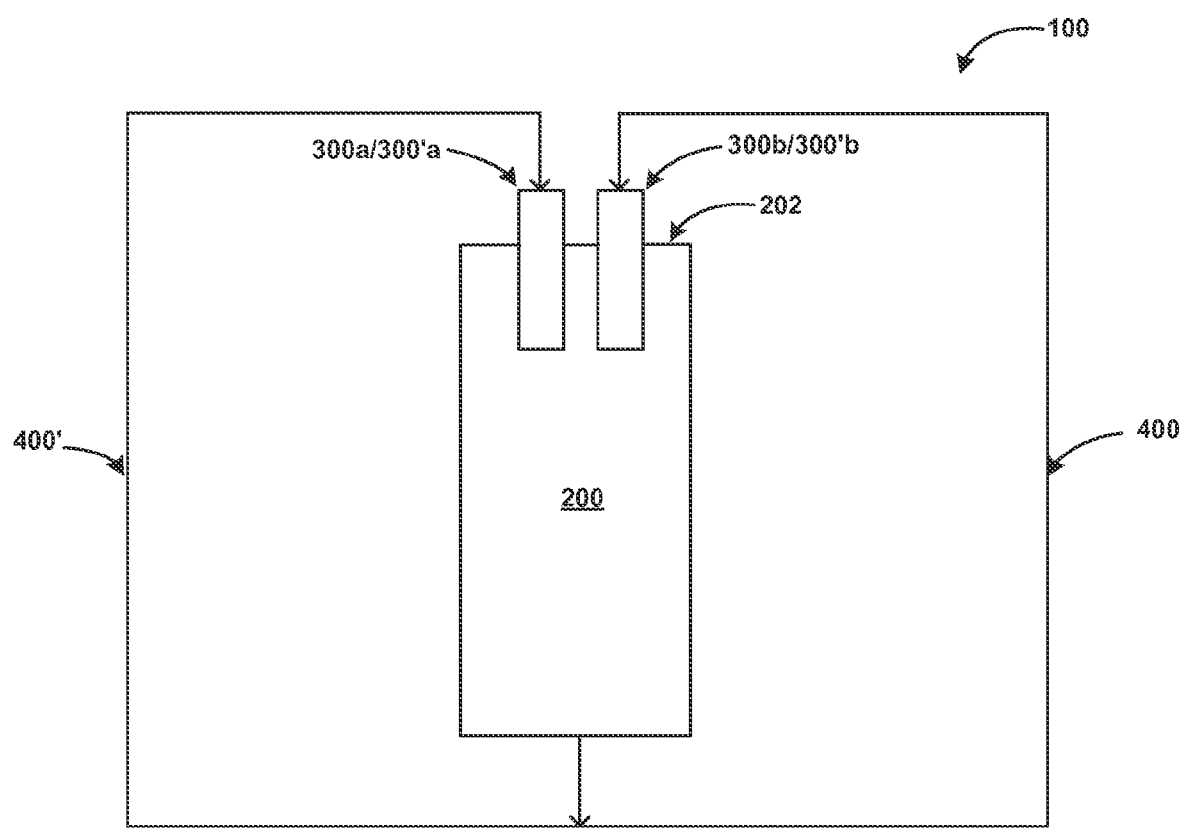

With reference to the drawings, FIGS. 1A-1D each schematically represents a system for ionic liquid catalyzed hydrocarbon conversion processes. With reference to FIG. 1A-1C, a system 100 for ionic liquid catalyzed hydrocarbon conversion may comprise a reactor vessel 200, at least one mixing device 300/300', and at least one circulation loop 400. Mixing device 300/300' provides for the rapid and thorough mixing of ionic liquid catalyst and hydrocarbon reactants. As an example, mixing device 300/300' may generate a large surface area of the ionic liquid catalyst phase in an ionic liquid/hydrocarbon mixture, thereby providing for the highly efficient performance of ionic liquid catalyzed hydrocarbon conversion processes.

Reactor vessel 200 has a reactor vessel top (or upper cap) 202, and mixing device 300/300' may be disposed at reactor vessel top 202. An upper (proximal) portion of mixing device 300/300' may extend proximally above reactor vessel top 202. A lower (distal) portion of mixing device 300/300' may be disposed within reactor vessel 200. Reactor vessel 200 may be at least substantially filled with liquid, and the portion of mixing device 300/300' within reactor vessel 200 may be immersed in the liquid contents of reactor vessel 200.

In an embodiment, reactor vessel 200 may be vertically aligned having a height greater than its width, and mixing device 300/300' may be disposed at reactor vessel top 202. In a sub-embodiment, mixing device 300/300' may be disposed vertically at reactor vessel top 202 such that the axis of each mixing device 300/300' may be at least substantially parallel to the axis of reactor vessel 200. In another sub-embodiment (not shown), mixing device(s) 300/300' may be disposed at various angles with respect to the axis of reactor vessel 200.

In an embodiment, reactor vessel 200 may be substantially cylindrical. In an embodiment, system 100 may comprise a plurality of mixing devices 300/300' per reactor vessel 200. As an example only, with further reference to FIG. 1B two mixing devices 300a/300'a and 300b/300'b are shown at reactor vessel top 202, it being understood that other numbers of mixing devices may similarly be used. In an embodiment, system 100 may comprise a plurality of mixing devices 300/300', wherein each of the mixing devices may be disposed at substantially the same elevation with respect to reactor vessel top 202.

Circulation loop 400 may be in fluid communication with reactor vessel 200 for withdrawing liquid (e.g., reactor effluent) from reactor vessel 200 into circulation loop 400. Mixing device 300/300' may be in fluid communication with reactor vessel 200. Circulation loop 400 may further be in fluid communication with mixing device 300/300' for recirculating the withdrawn liquid to reactor vessel 200 via mixing device 300/300'. In an embodiment, system 100 may comprise a plurality of circulation loops 400, wherein each circulation loop 400 may be in fluid communication with reactor vessel 200 and with at least one mixing device 300/300'. In embodiments of a system having a plurality of circulation loops 400, each circulation loop 400 may have a dedicated circulation pump and heat exchanger. In the embodiment of FIG. 1C, two circulation loops 400, 400' are shown, it being understood that other numbers of circulation loops may be used. In an embodiment, each of a plurality of circulation loops may have one or more dedicated mixing devices 300/300'.

Figure 1D:
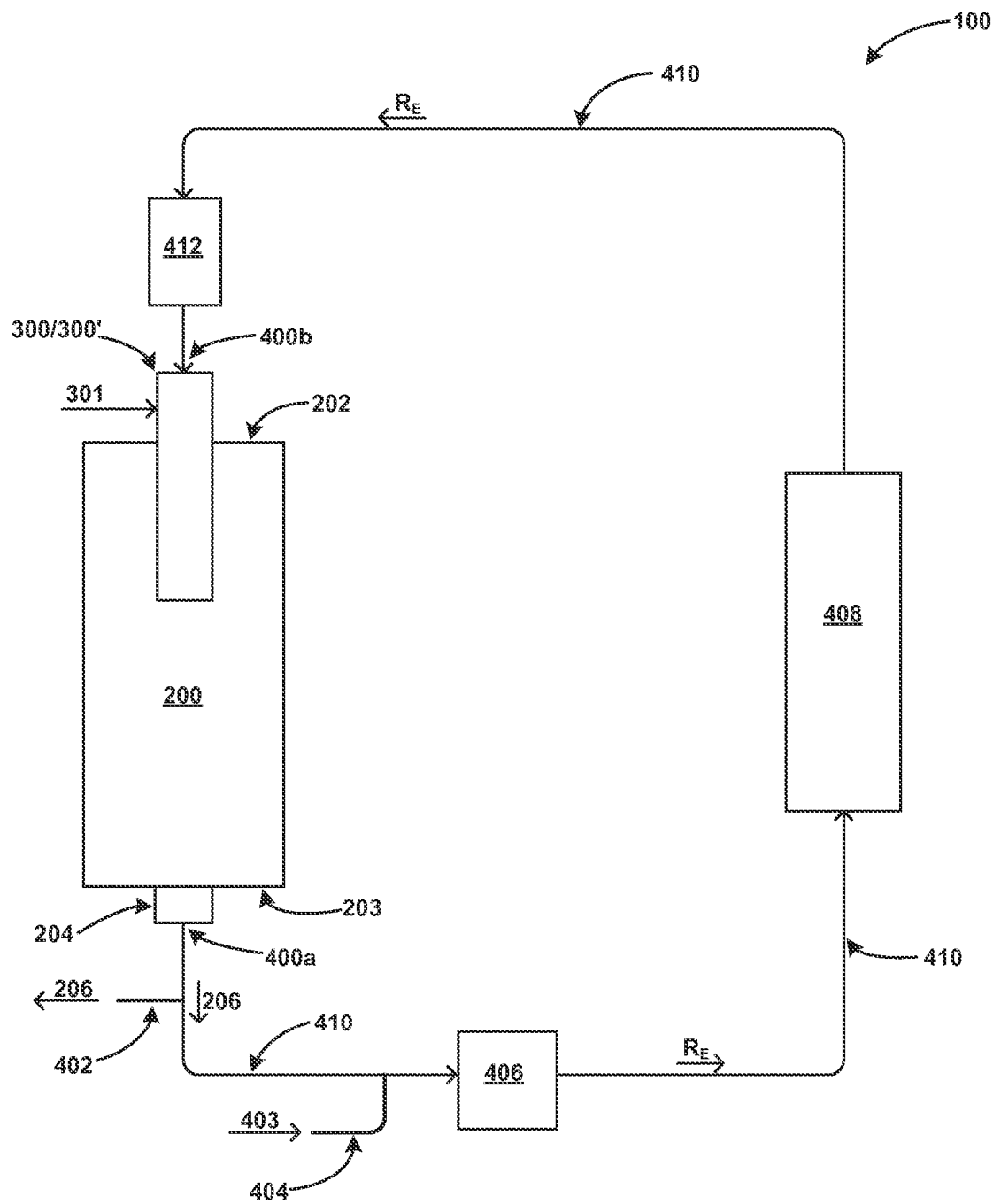

FIG. 1D schematically represents a system 100 comprising a reactor vessel 200 having a vessel outlet 204, a mixing device 300/300' disposed at reactor vessel top 202, and a circulation loop 400. In an embodiment, vessel outlet 204 may be at the opposite end of reactor vessel 200 from mixing device 300/300', e.g., vessel outlet 204 may be at the base (or lower cap) 203 of reactor vessel 200. A hydrocarbon feed 301 may be introduced into reactor vessel 200 via mixing device 300/300'. In an embodiment, the hydrocarbon feed may comprise an olefin feed stream, an isoparaffin feed stream, or a combination thereof, for ionic liquid catalyzed alkylation, e.g., as described hereinbelow.

Circulation loop 400 may comprise a first loop end 400a coupled to vessel outlet 204 and a second loop end 400b coupled to mixing device 300/300'. Circulation loop 400 may further comprise a loop outlet 402, an ionic liquid catalyst inlet 404, a circulation pump 406, and a heat exchanger 408. Circulation loop 400 may still further comprise at least one circulation loop conduit 410, e.g., for coupling components of circulation loop 400 to vessel outlet 204 and mixing device 300/300'.

Reactor effluent 206 may be withdrawn from reactor vessel 200 into circulation loop 400 via vessel outlet 204. Reactor effluent 206 may comprise ionic liquid catalyst that has previously contacted the hydrocarbon feed in reactor vessel 200. Fresh ionic liquid catalyst 403 may be added to reactor effluent 206, within circulation loop 400, via ionic liquid catalyst inlet 404 to provide an external recirculation stream, $R_E$. A portion of withdrawn reactor effluent 206 may be removed from circulation loop 400, via loop outlet 402, e.g., for fractionation thereof to provide an alkylate product. Loop outlet 402 and ionic liquid catalyst inlet 404 may be disposed at various locations within circulation loop 400 other than as shown in FIG. 1D.

With further reference to FIG. 1D, in an embodiment system 100 may further comprise a static mixer 412, in fluid communication with circulation loop 400, for premixing the external recirculation stream prior to introducing the external recirculation stream into mixing device 300/300'. In an embodiment, static mixer 412 may be disposed immediately upstream from, e.g., above, mixing device 300/300'. Although only one circulation loop 400 is shown in FIG. 1D, a plurality of circulation loops 400 may be used (see, for example, FIG. 1C). In an embodiment, system 100 may be configured for ionic liquid catalyzed alkylation reactions and processes. Feeds, ionic liquid catalysts, and reaction conditions for ionic liquid catalyzed alkylation are described hereinbelow.

Figure 2:
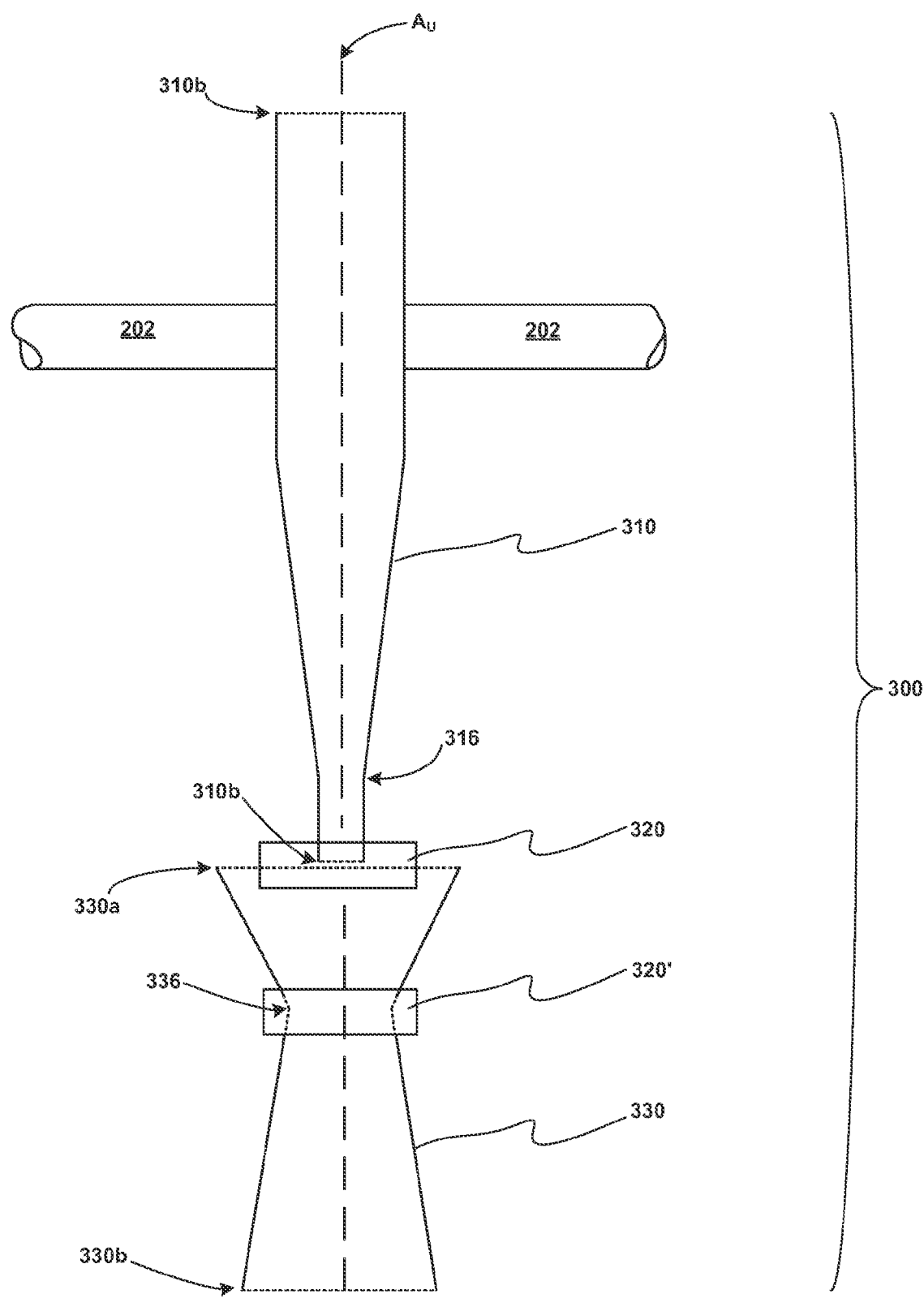
FIG. 2 schematically represents a mixing device having a feed injection array, as seen from the side, for an ionic liquid catalyzed hydrocarbon conversion system, according to an embodiment of the present invention.

FIG. 2 schematically represents a mixing device 300 comprising an upper venturi 310, at least one feed injection array 320, and a lower venturi 330. In an embodiment, each mixing device 300 may comprise a single upper venturi 310 and a single lower venturi 330. Each feed injection array 320 may comprise a plurality of feed injection nozzles 322 (see, e.g., FIGS. 5A-11B), such that each mixing device 300 may comprise a plurality of feed injection nozzles 322 per upper venturi 310/lower venturi 330. In an embodiment, upper venturi 310 may be disposed vertically within reactor vessel top 202. Upper venturi 310 may be affixed to, and sealingly engaged with, reactor vessel top 202.

In FIG. 2 the axis of upper venturi 310 is indicated by the line labeled $A_U$. Lower venturi 330 may be coaxial with upper venturi 310. In an embodiment, lower venturi 330 may be affixed to upper venturi 310, e.g., using suitable support structures (not shown), such as steel bars, and the like. Other mechanisms for affixing or anchoring lower venturi 330 relative to upper venturi 310 are also possible. In an embodiment, lower venturi proximal end 330a may be disposed at the same elevation or about the same elevation as upper venturi distal end 310b, e.g., as described with reference to FIG. 3B, infra. In FIG. 2, lower venturi proximal end 330a may be shown below upper venturi distal end 310b for the sake of clarity of illustration.

According to various embodiments, mixing device 300 may have a first feed injection array 320 at the same elevation or about the same elevation as lower venturi proximal end 330a, and/or mixing device 300 may have a second feed injection array 320' at the same elevation or about the same elevation as lower venturi constriction point 336, e.g., as described hereinabove and with respect to FIG. 4B, infra. Mixing device 300 is not limited to a particular number, arrangement, or location of feed injection array(s). As shown, lower venturi constriction point 336 may be at an elevation below lower venturi inlet 332 and above lower venturi outlet 334. In an embodiment, lower venturi constriction point 336 may be at an elevation in the range from 10% to 90% of the length, $L_L$, of lower venturi 330 below lower venturi inlet 332.

In an embodiment, upper venturi distal end 310b, feed injection array(s) 320/320', and lower venturi 330 may be disposed within reactor vessel 200. In an embodiment, feed injection array(s) 320/320' may be disposed coaxially with both upper venturi 310 and lower venturi 330. Feed injection array(s) 320/320' may be affixed, attached, or coupled to upper venturi 310 and/or to lower venturi 330, for example, according to the number, arrangement, and elevation of feed injection array(s) 320/320' relative to upper venturi 310 and lower venturi 330.

Figure 3B:
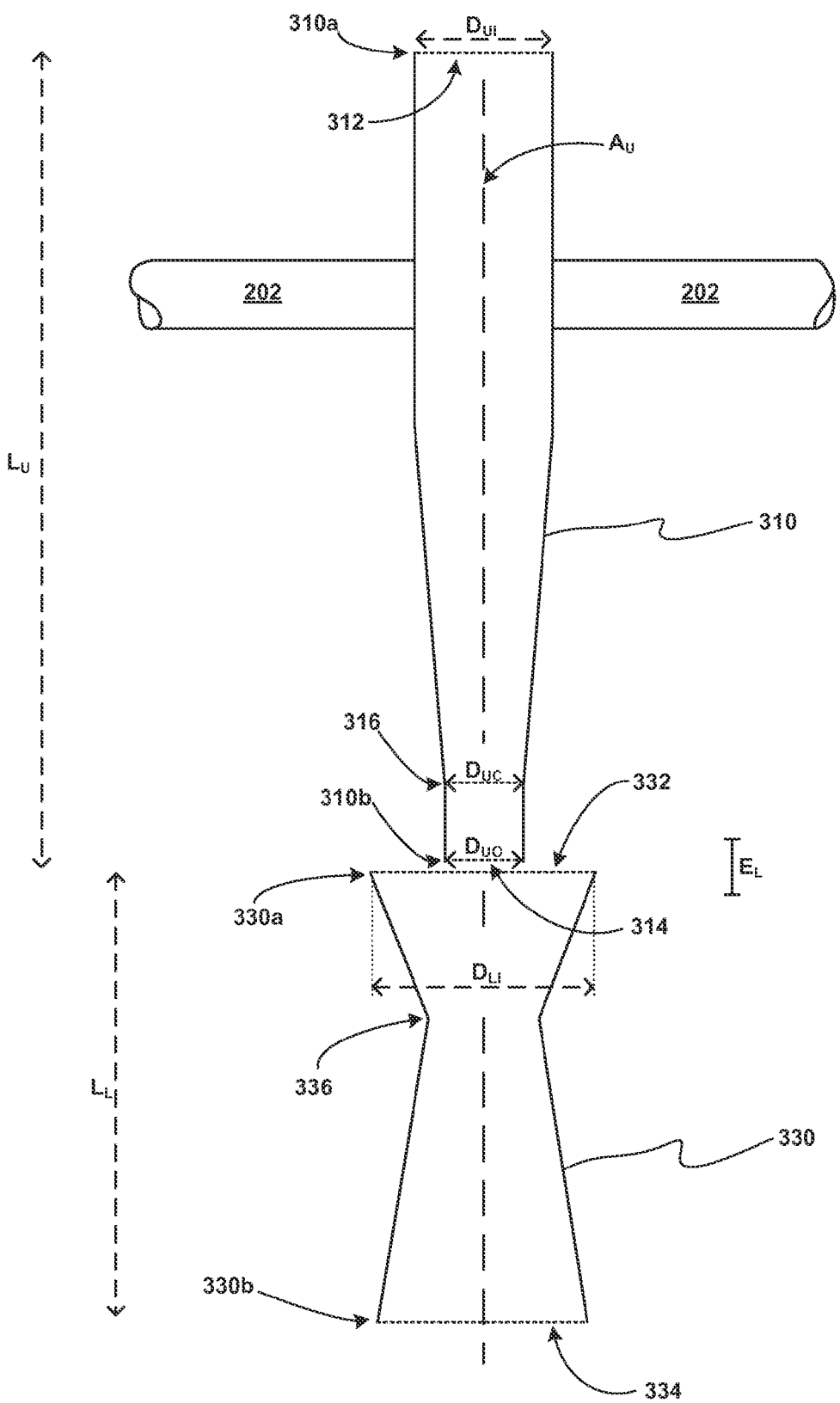
FIG. 3B schematically represents a mixing device in sectional view, according to an embodiment of the present invention.

FIG. 3A schematically represents an upper venturi for a mixing device in perspective view, and FIG. 3B schematically represents a mixing device in sectional view. FIG. 3C schematically represents an upper venturi in sectional view according to another embodiment. Upper venturi 310 is shown in isolation in FIG. 3A and feed injection array(s) 320 are omitted from FIG. 3B for the sake of clarity of illustration. With reference to FIGS. 3A-3B, upper venturi 310 may have an axial inlet 312 at upper venturi proximal end 310a and an axial outlet 314 at upper venturi distal end 310b. Each of upper venturi inlet 312 and upper venturi outlet 314 may be at least substantially circular. Upper venturi 310 may have a length $L_U$. Upper venturi inlet 312 and upper venturi outlet 314 have diameters $D_{UI}$ and $D_{UO}$, respectively. In an embodiment, the diameter, $D_{UI}$, of upper venturi inlet 312 may be greater than the diameter, $D_{UO}$, of upper venturi outlet 314 ($D_{UI} > D_{UO}$).

In an embodiment, the vertical bar, $E_L$, in FIG. 3B indicates a range of elevations for locating lower venturi inlet 332 relative to upper venturi outlet 314, wherein the distance corresponding to $E_L$ is vertically centered at the elevation of upper venturi outlet 314. In an embodiment, upper venturi outlet 314 is axial and the elevation of upper venturi outlet 314 corresponds to the elevation of upper venturi distal end 310b. Similarly, in an embodiment lower venturi inlet 332 is axial and the elevation of lower venturi inlet 332 corresponds to the elevation of lower venturi proximal end 330a. In FIGS.

3B and 4B, lower venturi proximal end 330a may be shown as being slightly below upper venturi distal end 310b for the sake of clarity of illustration.

With further reference to FIG. 3B, in an embodiment lower venturi proximal end 330a may be disposed at the same elevation or about the same elevation as upper venturi distal end 310b such that lower venturi proximal end 330a is disposed at an elevation within a range spanning a distance not greater than (≤) $0.5E_L$ above or below upper venturi distal end 310b, wherein the distance $E_L$ equals 20% of the diameter, $D_{LI}$, of the lower venturi inlet ($E_L = 0.2 D_{LI}$). In other embodiments, the distance $E_L$ may be equal to 50% of the diameter $D_{LI}$ ($E_L = 0.5 D_{LI}$) or 100% of the diameter $D_{LI}$ ($E_L = D_{LI}$). Other elevations of lower venturi inlet 332 relative to upper venturi outlet 314 are also possible.

Upper venturi 310 may further comprise a constriction point 316. Upper venturi constriction point 316 may be defined as the point or location along upper venturi 310 where its internal diameter, $D_{UC}$, has tapered to a minimum. As shown, upper venturi constriction point 316 may be at an elevation above upper venturi distal end 310b. Tapering of the internal diameter of upper venturi 310 may be linear, or non-linear, or a combination thereof. The relationship between liquid velocity and pressure changes in a venturi or venturi tube, e.g., according to the venturi effect, is well known in the art.

In an embodiment, one or more portions of upper venturi 310 may be at least substantially non-tapered; for example, a proximal portion and/or a distal portion of upper venturi 310 may be at least substantially cylindrical (see, for example, FIG. 3A). In an embodiment, the diameter, $D_{UO}$, of upper venturi outlet 314 may be the same or substantially the same as the internal diameter, $D_{UC}$, of upper venturi constriction point 316 ($D_{UO} = D_{UC}$). In another embodiment, upper venturi 310 may be flared distal to upper venturi constriction point 316, such that the diameter, $D_{UO}$, of upper venturi outlet 314 may be greater than the internal diameter, $D_{UC}$, of upper venturi constriction point 316 ($D_{UO} > D_{UC}$) (see, for example, FIG. 3C).

Figure 4B:
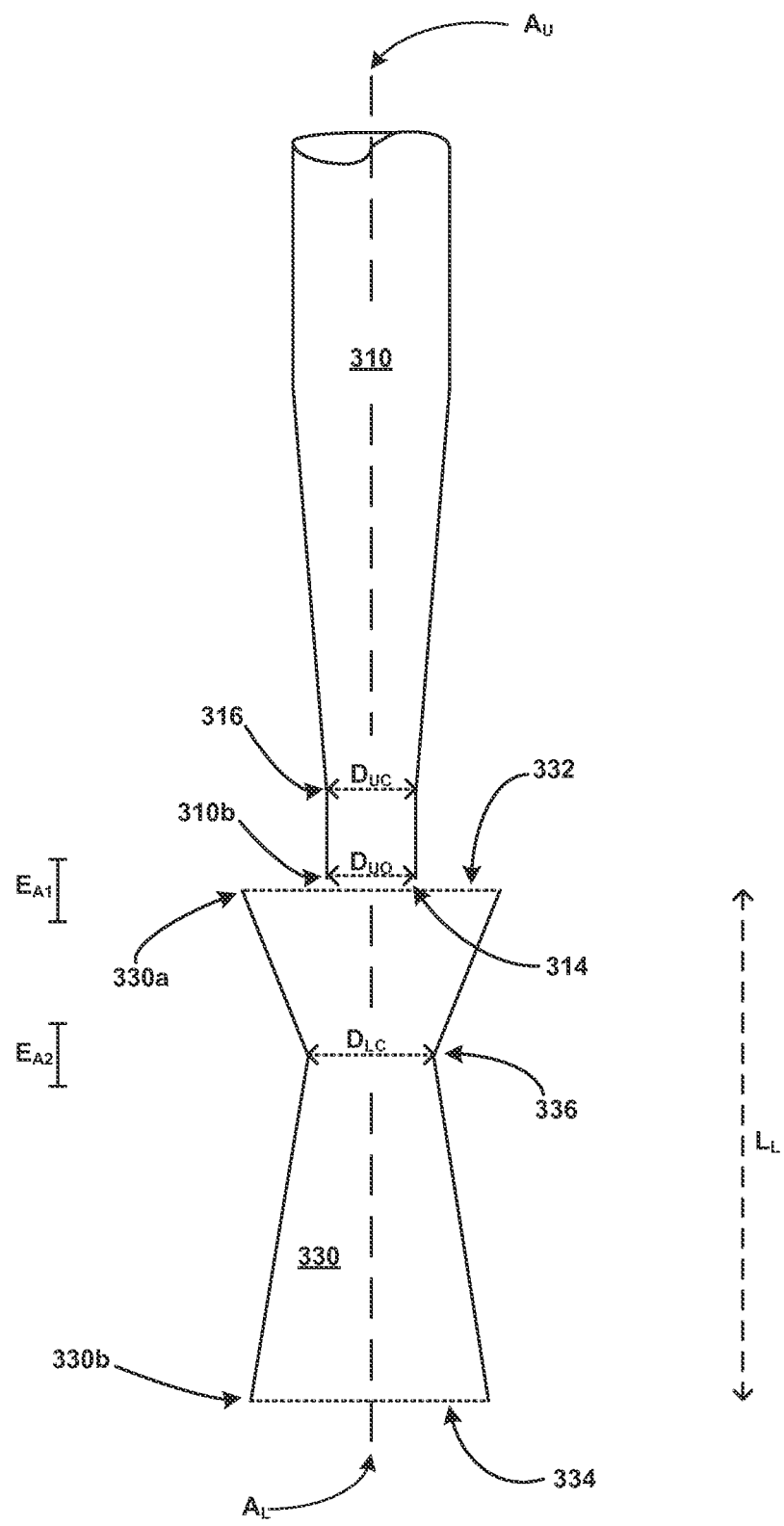
FIG. 4B schematically represents a lower venturi for a mixing device in sectional view in relation to an upper venturi outlet, according to an embodiment of the present invention.

FIG. 4A shows a lower venturi of a mixing device in perspective view, and FIG. 4B shows a lower venturi for a mixing device in sectional view in relation to an upper venturi outlet. FIG. 4C shows a lower venturi in sectional view according to another embodiment. With reference to FIGS. 4A-4C, lower venturi 330 may comprise an axial inlet 332 at lower venturi proximal end 330a and an axial outlet 334 at lower venturi distal end 330b. Each of lower venturi inlet 332 and lower venturi outlet 334 may be at least substantially circular. Lower venturi 330 may further comprise a constriction point 336. Lower venturi constriction point 336 may be defined as the location along lower venturi 330 where the internal diameter, $D_{LC}$, has tapered to a minimum. Tapering of the internal diameter of lower venturi 330 may be linear, or non-linear, or a combination thereof. In an embodiment, a portion of lower venturi 330 may be at least substantially non-tapered. As a non-limiting example, in an embodiment a portion of lower venturi 330 distal to lower venturi constriction point 336 may be at least substantially cylindrical (see, e.g., FIG. 4C).

With further reference to FIG. 4B, lower venturi 330 may have a length $L_L$. Lower venturi constriction point 336 may have an internal diameter $D_{LC}$, and upper venturi outlet 314 may have a diameter $D_{UO}$. According to various embodiments, the vertical bars labeled $E_{A1}$ and $E_{A2}$ (FIG. 4B) may each indicate a range of elevations for the location of feed injection array(s) 320/320' relative to lower venturi proximal end 330a and lower venturi constriction point 336, respectively. The distances corresponding to $E_{A1}$ and $E_{A2}$ are vertically centered at lower venturi proximal end 330a and lower venturi constriction point 336, respectively. The bar labeled $E_{A1}$ may be used to represent a distance (arbitrary units) relative to the diameter, $D_{UO}$, of upper venturi outlet 314, and the bar labeled $E_{A2}$ may be used to represent a distance (arbitrary units) relative to the internal diameter, $D_{LC}$, of lower venturi constriction point 336.

In an embodiment, mixing device 300 may have a single feed injection array 320 at an elevation within the bar labeled $E_{A1}$; in another embodiment, mixing device 300 may have a single feed injection array 320' at an elevation within the bar labeled $E_{A2}$; and in yet another embodiment, mixing device 300 may have a first feed injection array 320 at an elevation within the bar labeled $E_{A1}$ as well as a second feed injection array 320' at an elevation within the bar labeled $E_{A2}$.

In an embodiment, feed injection array 320 may be disposed at the same elevation or about the same elevation as lower venturi proximal end 330a such that feed injection array 320 is disposed at an elevation within a range spanning a distance not greater than ($\leq$) $0.5E_{A1}$ above or below lower venturi proximal end 330a, wherein $E_{A1}$ equals 20% of the diameter, $D_{UO}$, of upper venturi outlet 314. In other embodiments, the distance $E_{A1}$ may be equal to 50% of the diameter $D_{UO}$ ($E_{A1}=0.5D_{UO}$) or 100% of the diameter $D_{UO}$ ($E_{A1}=D_{UO}$).

In another embodiment, feed injection array 320' may be disposed at the same elevation or about the same elevation as lower venturi constriction point 336 such that feed injection array 320' is disposed at an elevation within a range spanning a distance not greater than ($\leq$) $0.5E_{A2}$ above or below lower venturi constriction point 336, wherein $E_{A2}$ equals 20% of the internal diameter, $D_{LC}$, of lower venturi constriction point 336. In other embodiments, the distance $E_{A2}$ may be equal to 50% of the internal diameter $D_{LC}$ ($E_{A2}=0.5D_{LC}$) or 100% of the internal diameter $D_{LC}$ ($E_{A2}=D_{LC}$). Elevations for feed injection array(s) 320, 320' other than those delineated by the bars $E_{A1}$ and $E_{A2}$ of FIG. 4B are also possible.

Figure 5A:
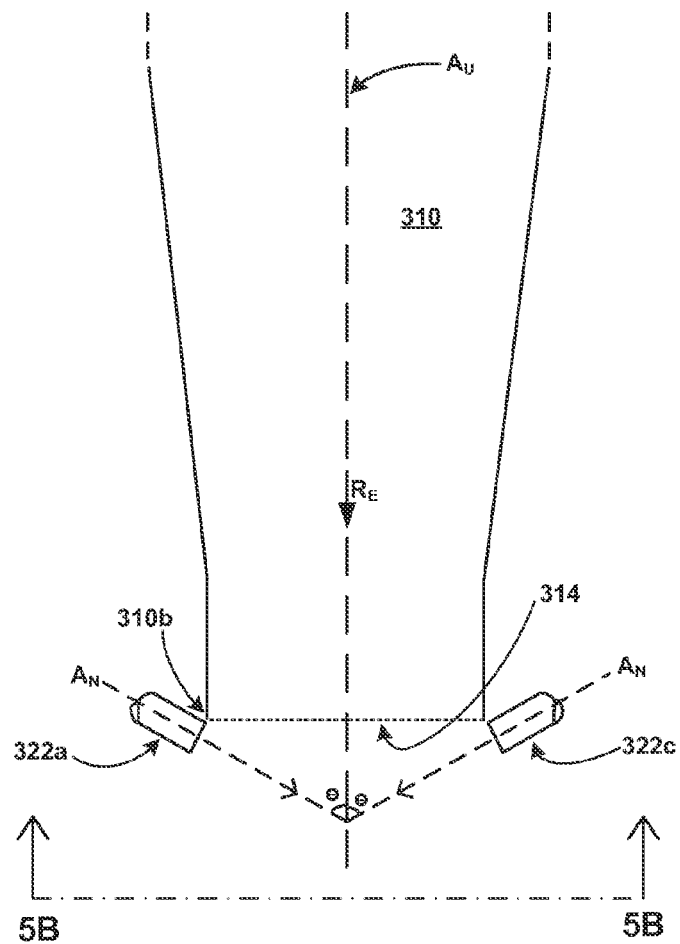
FIG. 5A shows the intersection of the axis of an upper venturi with the axis of each of a plurality of feed injection nozzles of a feed injection array.

In an embodiment, a feed injection array 320 for a mixing device 300 may be configured such that the axis of each of the plurality of feed injection nozzles 322 is at an angle in the range from 0° to 90° to the axis of upper venturi 310. FIG. 5A shows a distal (lower) portion of an upper venturi 310 in relation to a plurality of feed injection nozzles 322 of a feed injection array 320. In an embodiment, the angle, θ, between the axis, $A_N$, of each feed injection nozzle 322 and the axis, $A_U$, of upper venturi 310 may be greater than (>) 0° and not greater than ($\leq$) 90°, such that the axis of each feed injection nozzle 322 intersects the axis of upper venturi 310 at an elevation below upper venturi outlet 314. In a sub-embodiment, the angle of intersection, θ, may be in the range from 20° to 90°, or from 25° to 90°, or from 30° to 90°. In another sub-embodiment, the angle of intersection, θ, may be in the range from 80° to 90°, or from 85° to 90°, or at least substantially a right angle.

With further reference to FIG. 5A, the axes, $A_N$, of feed injection nozzles 322a and 322c may intersect the axis, $A_U$, of upper venturi 310 at a common intersection at an elevation below upper venturi outlet 314. In FIG. 5A, the arrow $R_E$ indicates the downward direction of the central jet from upper venturi 310.

Figure 5B:
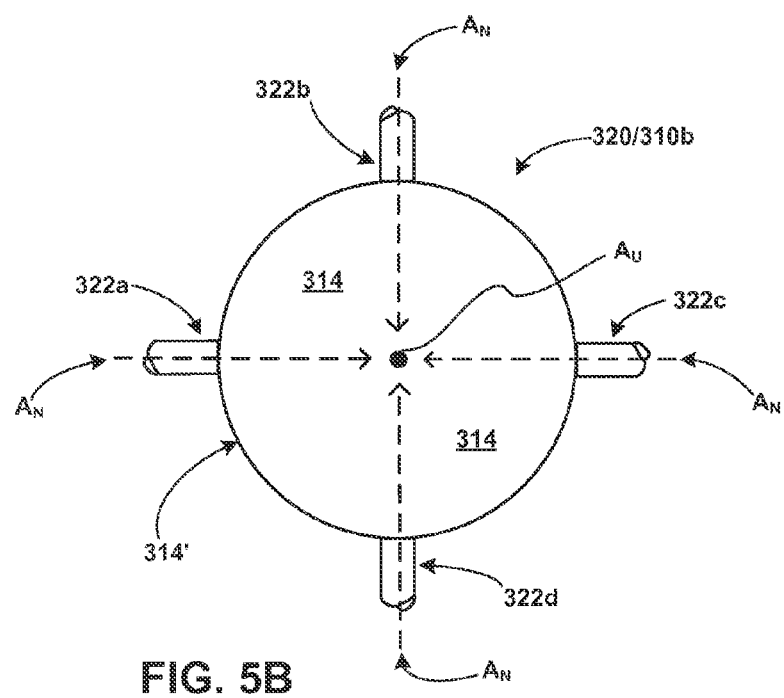
FIG. 5B shows the intersection of the axis of the upper venturi with the axis of each of the feed injection nozzles, as seen along the line 5B-5B of FIG. 5A, according to an embodiment of the present invention.

FIG. 5B shows the intersection of the axis of the upper venturi with the axis of each feed injection nozzle, as seen along the line 5B-5B of FIG. 5A. In FIG. 5B, the arrow on each of axes, $A_N$, indicates the direction of each lateral jet from feed injection nozzles 322a-d toward the axis, $A_U$, of upper venturi 310. As shown, each of feed injection nozzles 322a-d of a given feed injection array 320 may be spaced equi-radially from the axis, $A_U$, of upper venturi 310. FIG. 5B shows a feed injection array 320 having four evenly spaced feed injection nozzles 322a-d, e.g., for clarity of illustration. In practice, each feed injection array 320 may comprise other (e.g., greater) numbers, and other arrangements, of feed injection nozzles 322.

Figure 6A:
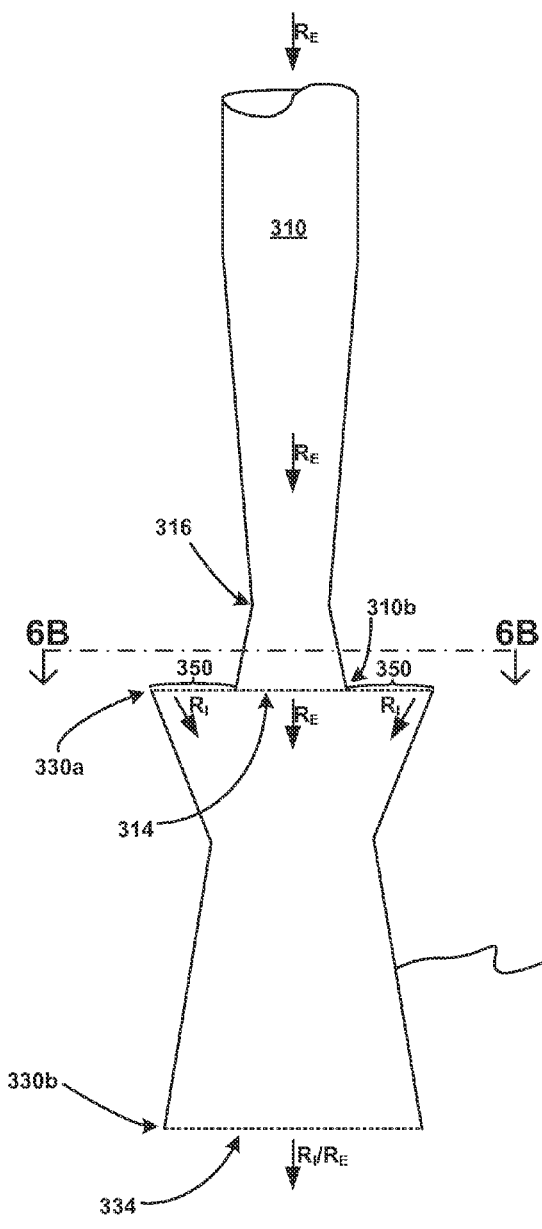
FIG. 6A shows, in sectional view, an inter-venturi channel in relation to an upper venturi and a lower venturi of a mixing device.
Figure 6B:
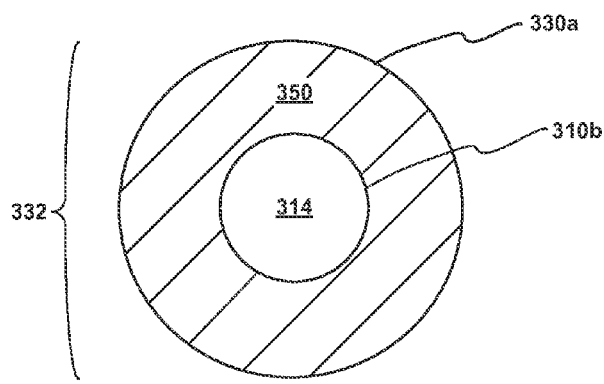
FIG. 6B shows the inter-venturi channel in relation to the upper venturi outlet and the lower venturi inlet as seen along the line 6B-6B of FIG. 6A, according an embodiment of the present invention.

FIG. 6A shows, in sectional view, an inter-venturi channel in relation to an upper venturi and a lower venturi of a mixing device 300, and FIG. 6B shows the inter-venturi channel in relation to the upper venturi outlet and the lower venturi inlet as seen along the line 6B-6B of FIG. 6A. Upper venturi 310 has an axial outlet 314 at upper venturi distal end 310b and lower venturi 330 has an axial inlet 332 at lower venturi proximal end 330a (see, for example, FIGS. 3A-4B). In an embodiment, lower venturi inlet 332 is spaced radially outward from upper venturi outlet 314 to define an inter-venturi channel 350 between lower venturi proximal end 330a and upper venturi distal end 310b. Each of lower venturi inlet 332 and upper venturi outlet 314 may be at least substantially circular. In an embodiment, inter-venturi channel 350 may be substantially annular (see, for example, FIG. 6B). In an embodiment, inter-venturi channel 350 allows the flow of an internal recirculation stream of reactor vessel 200, wherein the internal recirculation stream may flow downward through inter-venturi channel 350 into lower venturi 330 and out of lower venturi outlet 334.

With further reference to FIG. 6A, the flow of the internal recirculation stream through inter-venturi channel 350 is indicated by the arrows labeled $R_I$, while the external recirculation stream flowing from upper venturi outlet 314 is indicated by the arrows labeled $R_E$. The flow of the internal recirculation stream of reactor vessel 200, e.g., through inter-venturi channel 350 and lower venturi 330, may further promote mixing of the reactor contents comprising a multiphase reaction system, such as an emulsion of an ionic liquid catalyst in a hydrocarbon mixture. In an embodiment, the ratio of the flow rate (vol. per unit time) of the internal recirculation stream to the flow rate of the external recirculation stream may be in the range from 0.1 to 10, or from 0.2 to 5, or from 0.25 to 4.

Figure 7A:
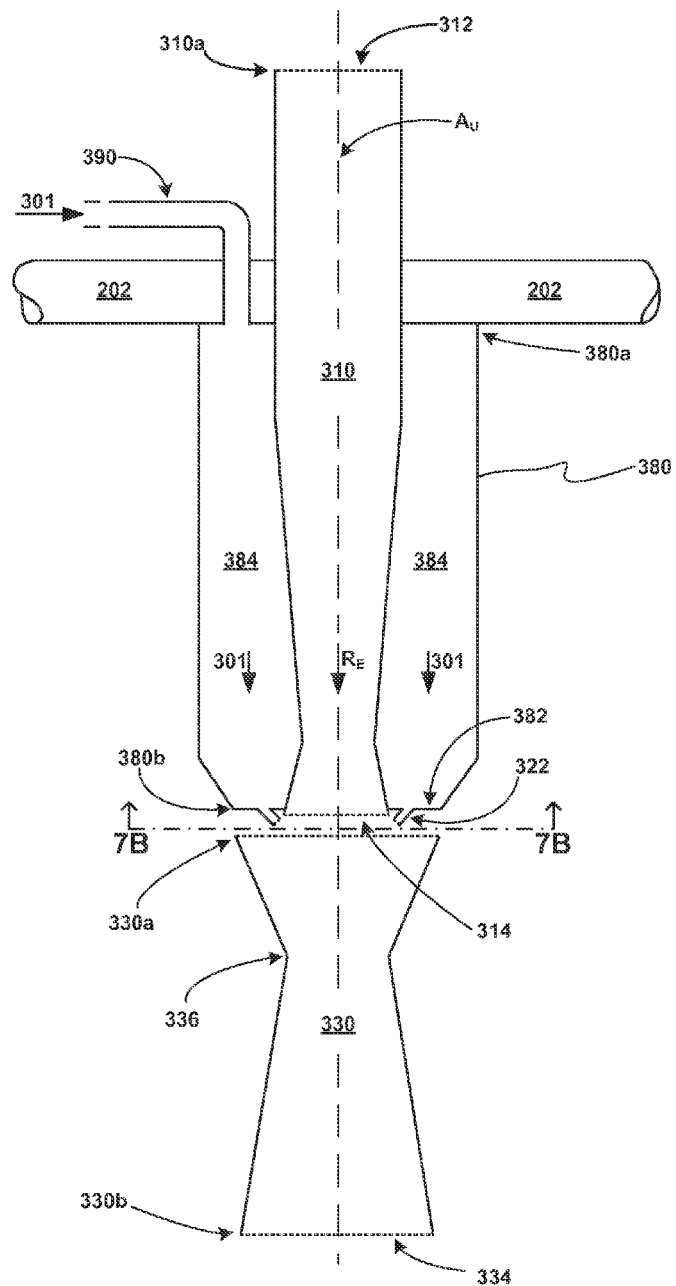
FIG. 7A schematically represents a mixing device, in sectional view.
Figure 7B:
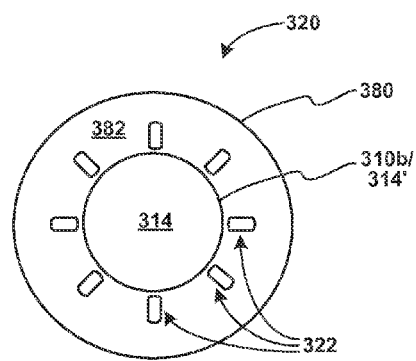
FIG. 7B shows a feed injection array of the mixing device as seen along the line 7B-7B of FIG. 7A, according an embodiment of the present invention.

FIG. 7A schematically represents a mixing device, in sectional view, and FIG. 7B shows a feed injection array of the mixing device as seen along the line 7B-7B of FIG. 7A. Mixing device 300 of FIGS. 7A-7B may comprise an upper venturi 310 and a lower venturi 330, e.g., as described with reference to FIGS. 3A-4B. Mixing device 300 may be disposed in reactor vessel 200 in a vertical orientation such that only a proximal portion of upper venturi 310 is disposed above reactor vessel top 202. A distal portion of upper venturi 310 may be disposed below reactor vessel top 202 and sealingly engaged therewith.

With further reference to FIGS. 7A-7B, mixing device 300 may comprise a jacket 380 surrounding a distal portion of upper venturi 310. Jacket 380 may be disposed radially outward from upper venturi 310 to define an annular feed conduit 384. Jacket 380 may have a jacket proximal end 380a. In an embodiment, jacket proximal end 380a may be sealingly engaged with the underside of reactor vessel top 202. Jacket 380 may include a jacket base 382 at jacket distal end 380b. Jacket base 382 may be sealed against upper venturi 310 at, or adjacent to, upper venturi distal end 310b. A plurality of feed injection nozzles 322 may extend distally of jacket base 382 to define a feed injection array 320 (see, for example, FIG. 7B). Feed conduit 384 may be in fluid communication with a feed supply line 390 for receiving hydrocarbon feed 301, and each feed injection nozzle 322 may be in fluid communication with feed conduit 384 for the projection of a lateral jet of the hydrocarbon feed from each of feed injection nozzles 322. In an embodiment, each lateral jet of hydrocarbon feed may be projected toward the upper venturi axis, $A_U$, such that each lateral jet collides with the central jet projected from upper venturi outlet 314. Mixing devices for system 100 as disclosed herein are not limited to a particular feed conduit configuration.

With further reference to FIG. 7B, in an embodiment feed injection nozzles 322 may be arranged so as to provide an annular and/or symmetrical feed injection array 320. Each feed injection nozzle 322 of feed injection array 320 may have a nozzle outlet 324 (see, for example, FIGS. 9A and 11A-11B). Although nozzles 322 are shown in FIG. 7B as terminating radially outward from the perimeter 314' of upper venturi outlet 314, in other embodiments feed injection nozzles 322 may extend radially inward to, or beyond, the perimeter 314' of upper venturi outlet 314.

Without reference to a particular figure or embodiment, mixing device 300 may be configured for projecting a central jet of an external recirculation stream (arrow $R_E$) downward from upper venturi outlet 314 into lower venturi 330. In an embodiment, the flow rate of the external recirculation stream may be in the range from 2 to 50 times the flow rate of hydrocarbon feed 301, or from 2 to 25 times the flow rate of hydrocarbon feed 301, or from 4 to 10 times the flow rate of hydrocarbon feed 301. In an embodiment, upper venturi 310 may be configured, e.g., suitably tapered, such that a pressure drop across upper venturi outlet 314 may be up to about 110 psi; in a sub-embodiment the pressure drop across upper venturi outlet 314 may be in the range from 10 to 110 psi, or from 50 to 80 psi. It is to be understood that the drawings are schematic representations that may not be drawn to scale and do not represent a specific design of the upper venturi or other components.

The external recirculation stream, $R_E$, supplied to upper venturi inlet 312 may comprise ionic liquid catalyst in combination with unreacted hydrocarbons. In an embodiment, the pressure drop across upper venturi outlet 314 may produce an ionic liquid/hydrocarbon emulsion comprising small to microscopic droplets of the ionic liquid catalyst, e.g., having an ionic liquid catalyst droplet diameter in the range from 1 to 1000 microns, or from 5 to 250 microns, or from 10 to 150 microns. Thus, the central jet of the external recirculation stream projected from upper venturi outlet 314 may comprise such an emulsion having small to microscopic droplets of the ionic liquid catalyst dispersed in the unreacted hydrocarbons. Such droplets may provide not only an ionic liquid catalyst surface area that will produce a high rate of reaction and a high quality product (e.g., alkylate), but also a hydrocarbon/ionic liquid mixed phase that is conducive to subsequent phase separation downstream.

FIG. 8A schematically represents a portion of a mixing device, in sectional view, and FIG. 8B shows a feed injection array of the mixing device, as seen along the line 8B-8B of FIG. 8A. Embodiments represented by FIGS. 8A-8B may have certain elements, features, and characteristics as described hereinabove, e.g., with reference to FIGS. 7A-7B. Lower venturi 330 is omitted from FIG. 8A for the sake of clarity. In an embodiment represented by FIGS. 8A-8B, feed injection array 320 may be configured such that the axis, $A_N$, of each feed injection nozzle 322 intersects the axis, $A_U$, of upper venturi 310 at an angle, $\theta$, of about 90° or substantially at a right angle. Accordingly, in an embodiment the axis, $A_N$, of each feed injection nozzle 322 may be at least substantially parallel to a plane defined by upper venturi outlet 314. Embodiments in which the axis of each feed injection nozzle 322 is orthogonal, or at least substantially orthogonal, to the axis of upper venturi 310 are not restricted to any particular feed conduit configuration(s).

In an embodiment, e.g., as shown in FIGS. 8A-8B, each feed injection nozzle 322 may terminate at a location radially inward from the perimeter 314' of upper venturi outlet 314, such that the central jet projected from upper venturi outlet 314 may collide with at least a terminal portion of each feed injection nozzle 322. Although feed injection nozzles 322 are shown in FIG. 8B as extending radially inward of the perimeter 314' of upper venturi outlet 314, in other embodiments feed injection nozzles 322 may terminate radially outward from perimeter 314' of upper venturi outlet 314, or feed injection nozzles 322 may terminate equi-radially with perimeter 314' of upper venturi outlet 314.

Figure 9A:
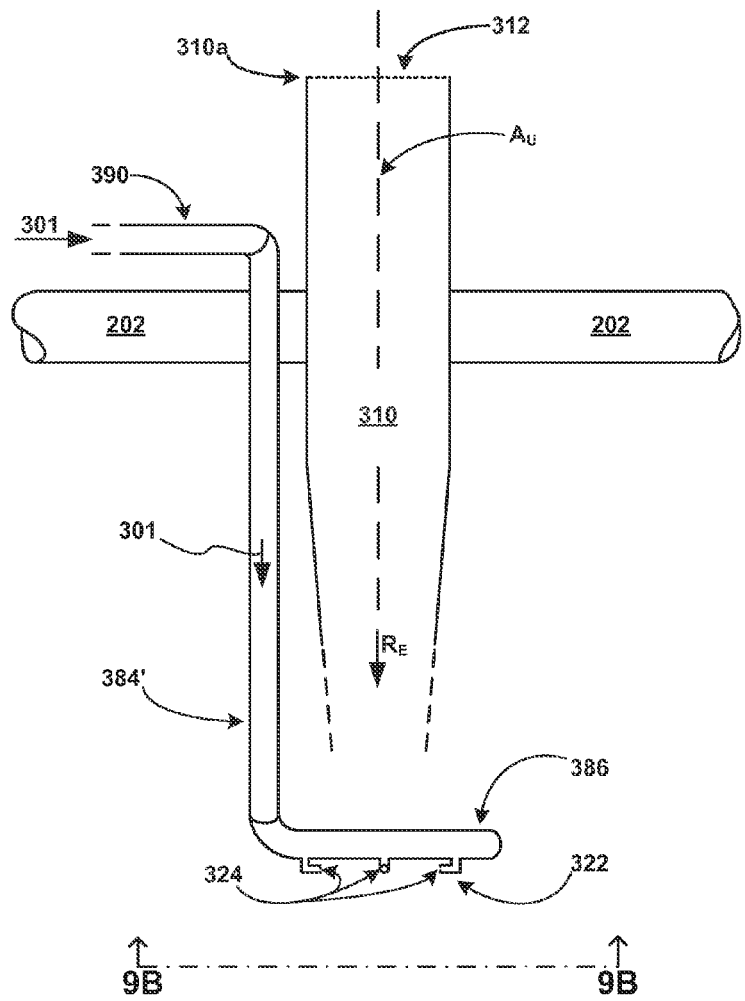
FIG. 9A schematically represents a portion of a mixing device.
Figure 9B:
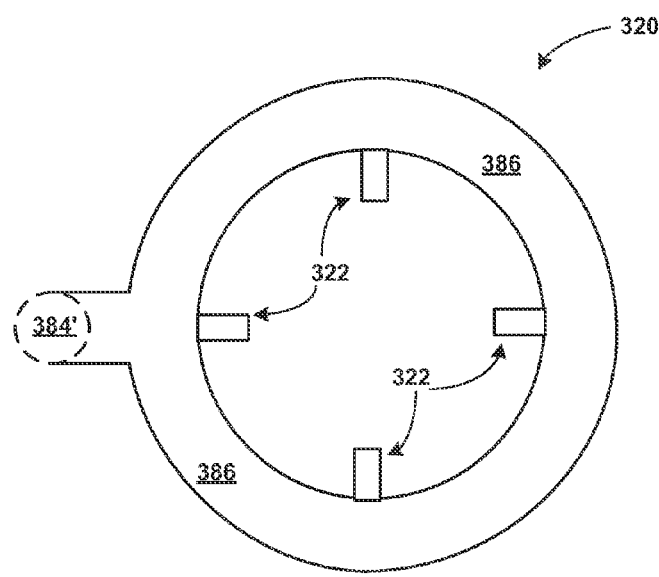
FIG. 9B shows a feed injection array of the mixing device, as seen along the line 9B-9B of FIG. 9A, according an embodiment of the present invention.

FIG. 9A schematically represents a portion of a mixing device, and FIG. 9B is an enlarged view showing a feed injection array of the mixing device as seen along the line 9B-9B of FIG. 9A. In FIG. 9A lower venturi 330 is omitted and the upper venturi 310 is truncated for the sake of clarity of illustration. Mixing device 300 may be disposed in reactor vessel 200 in a vertical orientation such that only a proximal portion of upper venturi 310 is disposed above reactor vessel top 202.

With further reference to FIGS. 9A-9B, in an embodiment mixing device 300 may comprise a feed injection array 320 comprising a plurality of feed injection nozzles 322. Each feed injection nozzle 322 may be in fluid communication with a feed injection manifold 386. In an embodiment, feed injection manifold 386 may be at least substantially annular. Feed injection manifold 386 may be in fluid communication with a feed supply line 390, e.g., via a tubular feed conduit 384', for distributing hydrocarbon feed to each of feed injection nozzles 322. In an embodiment, feed injection nozzles 322 may extend distally of (below) feed injection manifold 386. In an embodiment, tubular feed conduit 384' may be disposed laterally of upper venturi 310.

With further reference to FIG. 9B, in an embodiment feed injection nozzles 322 may be arranged so as to provide an annular and/or symmetrical feed injection array 320. As shown in FIG. 9A, each feed injection nozzle 322 may have a nozzle outlet 324 for the projection therefrom of a lateral jet of hydrocarbon feed. In an embodiment, a nozzle outlet 324 may be axially located at the terminus 322' of each feed injection nozzle 322 (see, for example, FIGS. 11A-11B). In an embodiment, each lateral jet may be projected toward the axis of upper venturi 310, such that each lateral jet collides with a central jet of liquid projected from upper venturi outlet 314.

Figure 10:
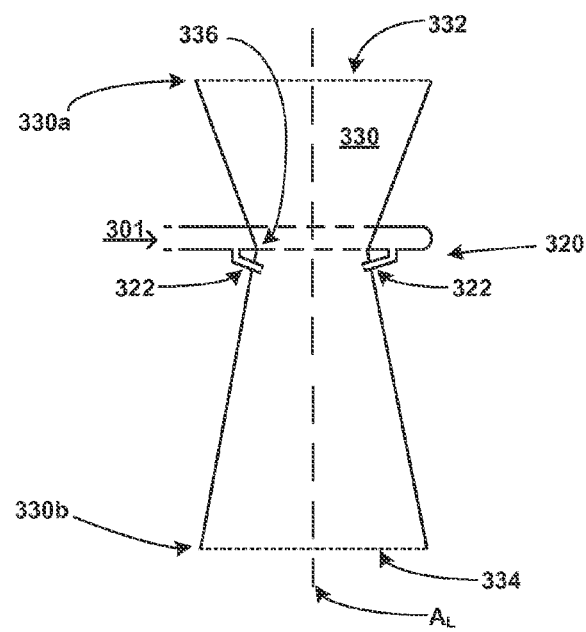
FIG. 10 schematically represents, in sectional view, a lower venturi for a mixing device having a feed injection array at the same elevation or about the same elevation as a constriction point of the lower venturi, according an embodiment of the present invention.

FIG. 10 schematically represents, in sectional view, a lower venturi for a mixing device having a feed injection array at the same elevation or about the same elevation as a constriction point of the lower venturi. Lower venturi 330 may have an axial inlet 332 at lower venturi proximal end 330a and an axial outlet 334 at lower venturi distal end 330b. Lower venturi 330 may further have a lower venturi constriction point 336, wherein lower venturi constriction point 336 may be disposed between lower venturi proximal end 330a and lower venturi distal end 330b, i.e., at an elevation below lower venturi inlet 332 and above lower venturi outlet 334. A feed injection array 320 may be disposed at the same elevation or about the same elevation as lower venturi constriction point 336. Feed injection array 320 may comprise a plurality of feed injection nozzles 322. Each feed injection nozzle 322 may be in fluid communication with a feed conduit (see, e.g., FIG. 9A) for supplying hydrocarbon feed to feed injection nozzles 322.

With further reference to FIG. 10, each feed injection nozzle 322 may extend into the interior of lower venturi 330. Each feed injection nozzle 322 may project a lateral jet of hydrocarbon feed, into lower venturi 330, at the same elevation or about the same elevation as lower venturi constriction point 336. Liquid flowing through lower venturi 330, e.g., a mixture of the internal- and external recirculation streams of the reactor vessel, may collide with each lateral jet of feed injection array 320. In an embodiment, liquid flowing through lower venturi 330 may also collide with a terminal portion of each feed injection nozzle 322. Feed injection array 320 may be configured such that the axis of each feed injection nozzle 322 may intersect the axis, $A_L$, of lower venturi 330, substantially as described with reference to FIGS. 5A-5B, supra, wherein lower venturi 330 may be coaxial with upper venturi 310. Two feed injection nozzles are shown in FIG. 10 for the sake of clarity of illustration; in practice, feed injection array 320 may comprise a greater number of annularly arranged feed injection nozzles 322, e.g., as described hereinabove.

Figure 11A:
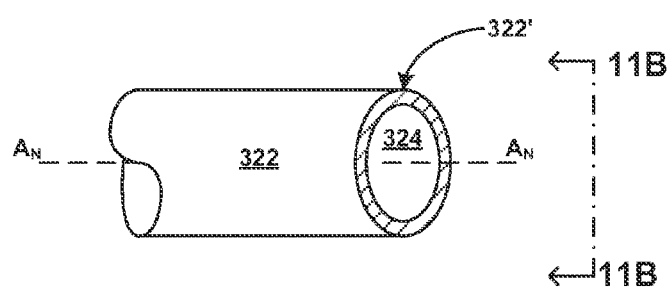
FIG. 11A shows, in perspective view, a terminal portion of a feed injection nozzle.
Figure 11B:
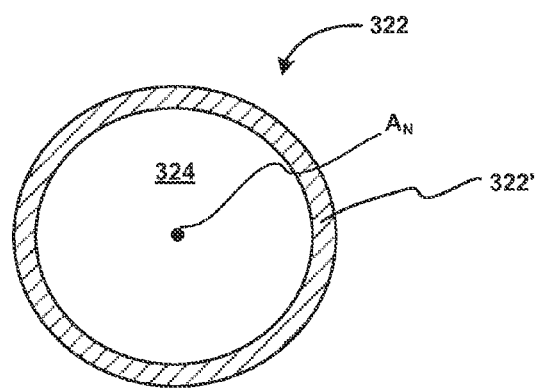
FIG. 11B shows a nozzle outlet of a feed injection nozzle as seen along the line 11B-11B of FIG. 11A, according an embodiment of the present invention.

FIG. 11A shows, in perspective view, a terminal portion of a feed injection nozzle 322, and FIG. 11B is an enlarged view of a nozzle outlet 324 of feed injection nozzle 322 as seen along the line 11B-11B of FIG. 11A. In an embodiment, nozzle outlet 324 may be axially disposed at the terminus 322' of feed injection nozzle 322, such that the center of nozzle outlet 324 coincides with the axis, $A_N$, of feed injection nozzle 322. In an embodiment, nozzle outlet 324 may be at least substantially circular or round. Other configurations and shapes for feed injection nozzles 322 and nozzle outlets 324 are also possible.

In the case of a feed injection array 320 disposed at the same elevation or about the same elevation as the lower venturi proximal end 330a, the terminus 322' of each feed injection nozzle 322 may be at the same radial location or about the same radial location as the perimeter 314' of the upper venturi outlet 314. In this context, the expression "the same radial location or about the same radial location" means that terminus 322' of each feed injection nozzle 322 may be disposed within a radial distance not greater than (≤) $0.2D_{UO}$ radially inward or radially outward from the perimeter 314' of upper venturi outlet 314 (see, e.g., FIGS. 7B and 8B), wherein $D_{UO}$ is the diameter of upper venturi outlet 314 (see, e.g., FIG. 4B).

In the case of a feed injection array 320 disposed at the same elevation or about the same elevation as the lower venturi constriction point 336, the terminus 322' of each feed injection nozzle 322 may be spaced radially outward from the lower venturi axis, $A_L$, by a distance in the range from 0.2 to $0.5D_{LC}$, or from $0.4D_{LC}$ to $0.5D_{LC}$, wherein $D_{LC}$ is the internal diameter of the lower venturi constriction point 336.

For a given feed injection array 320, all of the nozzle outlets 324 may be at the same elevation or substantially the same elevation (see, e.g., FIG. 9A). In this disclosure and the appended claims, the elevation of a given feed injection array, e.g., relative to the lower venturi, may be defined as, or referenced to, the elevation of the center of nozzle outlets 324 of that feed injection array.

Figure 12A:
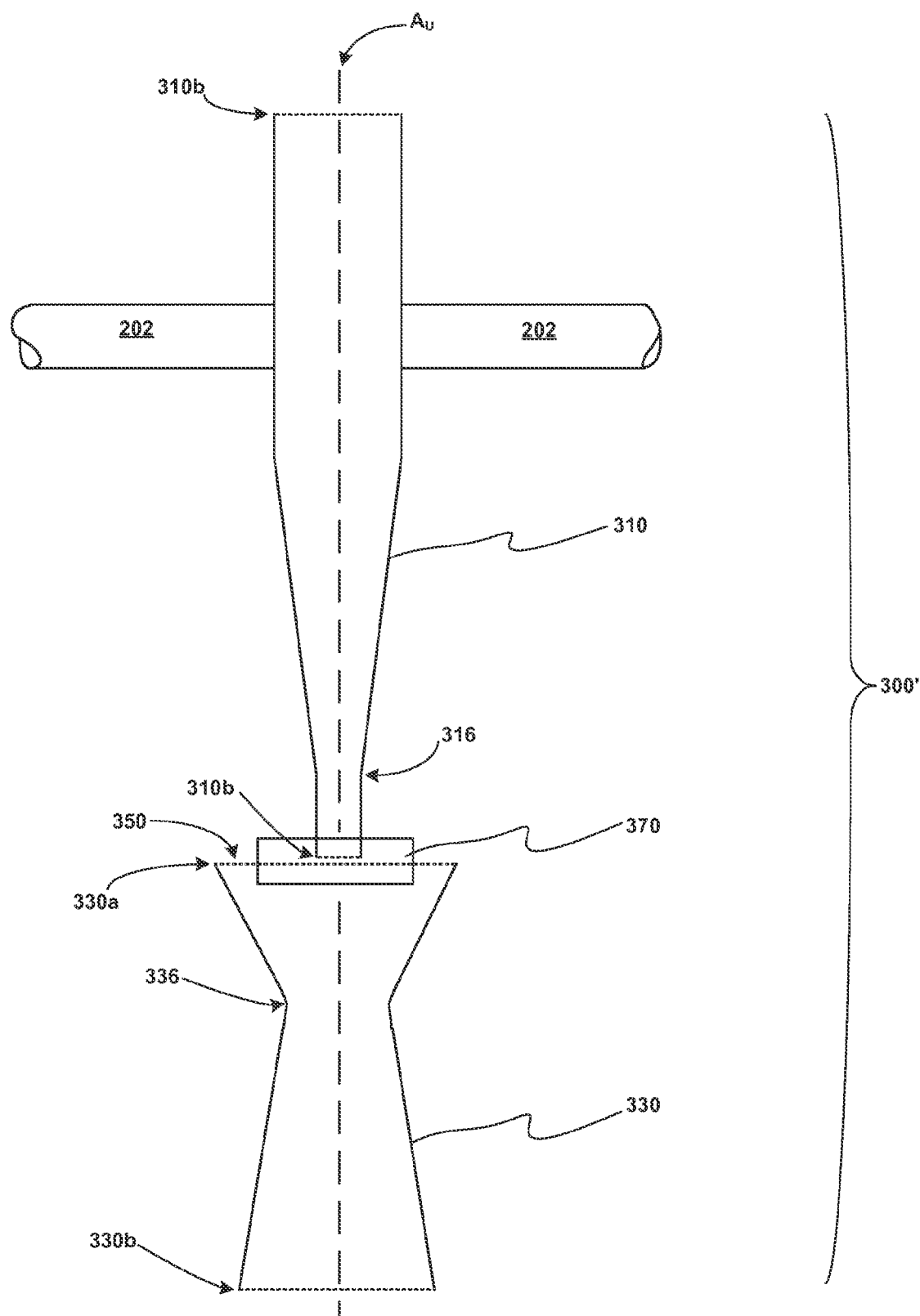
FIG. 12A schematically represents a mixing device having a feed injection annulus, as seen from the side, for an ionic liquid catalyzed hydrocarbon conversion system, according to an embodiment of the present invention.

FIG. 12A schematically represents a mixing device 300' comprising an upper venturi 310, a feed injection annulus 370, and a lower venturi 330. In an embodiment, upper venturi 310 may be disposed vertically within reactor vessel top 202. Upper venturi 310 may be affixed to, and sealingly engaged with, reactor vessel top 202.

In FIG. 12A the axis of upper venturi 310 is indicated by the line labeled $A_U$. Lower venturi 330 may be coaxial with upper venturi 310. In an embodiment, lower venturi 330 may be affixed to upper venturi 310, e.g., using suitable support structures (not shown), such as steel bars, and the like. In an embodiment, lower venturi proximal end 330a may be disposed at the same elevation or about the same elevation as upper venturi distal end 310b, e.g., as described hereinabove (see, for example, FIG. 3B). In FIG. 12A, lower venturi proximal end 330a may be shown below upper venturi distal end 310b for the sake of clarity of illustration.

In an embodiment, feed injection annulus 370 may be at the same elevation or about the same elevation as lower venturi proximal end 330a, e.g., as described hereinabove (see, for example, FIG. 4B). Mixing device 300' is not limited to a particular elevation or location of feed injection annulus 370. In an embodiment, upper venturi distal end 310b, feed injection annulus 370, and lower venturi 330 may be disposed within reactor vessel 200. In an embodiment, feed injection annulus 370 may be disposed coaxially with both upper venturi 310 and lower venturi 330. Feed injection annulus 370 may be affixed, attached, or coupled to upper venturi 310 and/or to lower venturi 330.

Figure 12B:
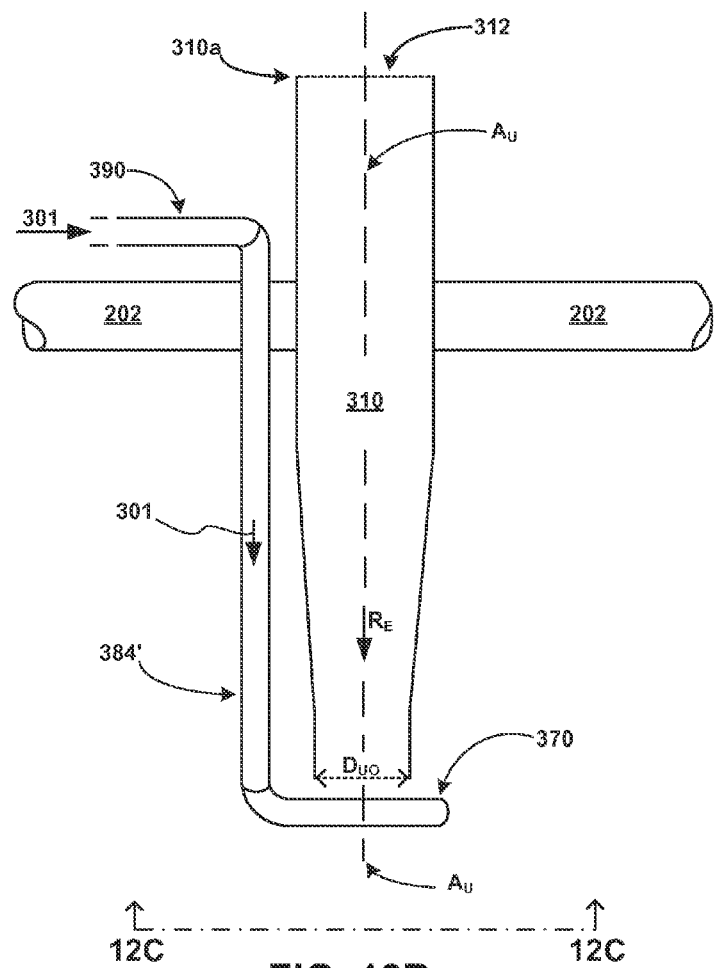
FIG. 12B schematically represents a portion of a mixing device having a feed injection annulus.
Figure 12C:
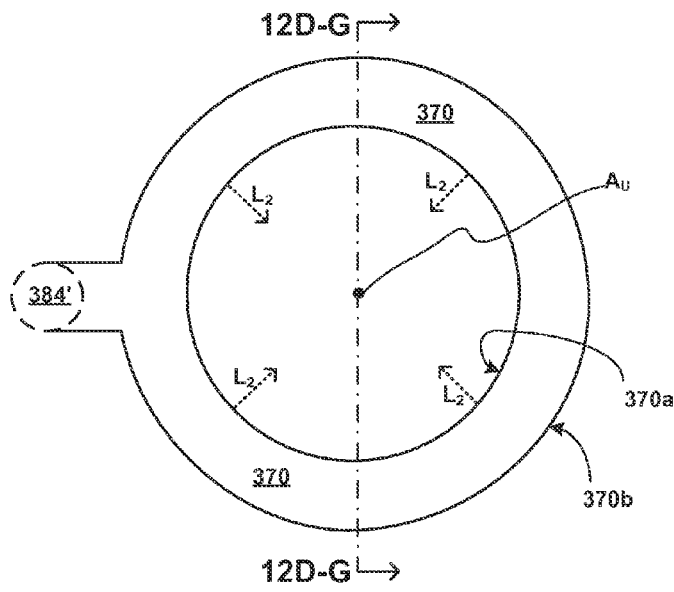
FIG. 12C shows the feed injection annulus as seen along the line 12C-12C of FIG. 12B, and FIGS. 12D-12G each show a feed injection annulus, as seen in sectional view along the line 12D-G-12D-G of FIG. 12C, according to various embodiments of the present invention.

FIG. 12B schematically represents a portion of a mixing device 300' having a feed injection annulus 370, FIG. 12C shows the feed injection annulus 370 as seen along the line 12C-12C of FIG. 12B, and FIGS. 12D-12G each show a feed injection annulus 370 as seen in sectional view along the line 12D-G-12D-G of FIG. 12C according various embodiments. In FIG. 12B lower venturi 330 is omitted for the sake of clarity of illustration. In an embodiment, mixing device 300' may be disposed in reactor vessel 200 in a vertical orientation such that only a proximal portion of upper venturi 310 is disposed above reactor vessel top 202.

With further reference to FIGS. 12B-12C, feed injection annulus 370 may be in fluid communication with a feed supply line 390, e.g., via a tubular feed conduit 384', for providing hydrocarbon feed 301 to mixing device 300'. In an embodiment, tubular feed conduit 384' may be disposed laterally of upper venturi 310. Feed injection annulus 370 may have an annulus inner portion 370a and an annulus outer portion 370b. Each feed injection annulus 370 may have one or more feed injection ports 372 at annulus inner portion 370a (see, e.g., FIGS. 12D-12G).

With reference to FIGS. 12B-12G, feed injection annulus 370 may be configured so as to provide an annular and/or symmetrical projection of a second liquid from at least one feed injection port 372 toward the axis, $A_U$, of upper venturi 310. In an embodiment, feed injection annulus 370 may be configured such that the second liquid is projected from the at least one feed injection port 372 as at least one jet that collides with a central jet of a first liquid projected from upper venturi distal end 310b. According to an embodiment, the projection of the second liquid from feed injection annulus 370 toward upper venturi axis, $A_u$, may be indicated in FIG. 12C by the arrows labeled $L_2$. According to various sub-embodiments, the arrows labeled $L_2$ in FIG. 12C may represent a single (e.g., annular) jet, or a plurality of up to four jets, or a plurality of more than four jets of the second liquid.

Figure 12D:
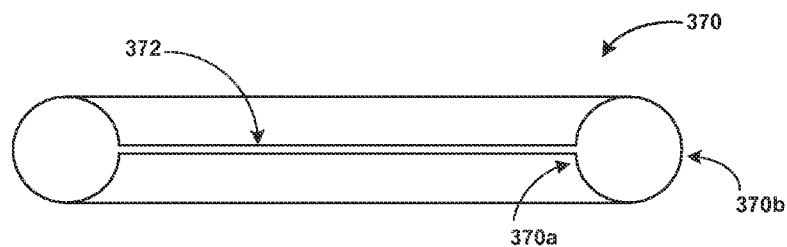
Figure 12E:
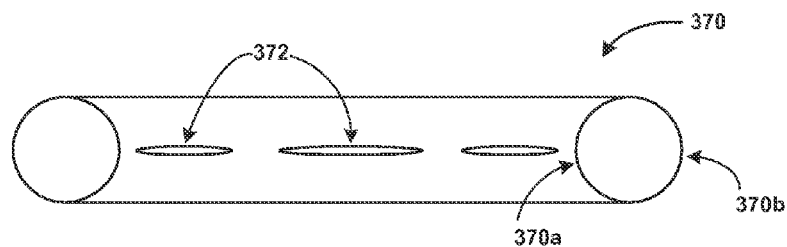
Figure 12F:
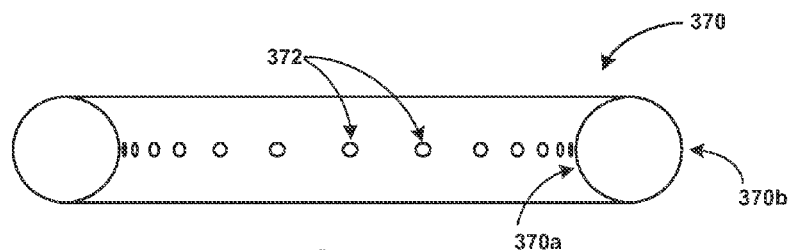

FIG. 12D is a sectional view of a feed injection annulus 370 having a feed injection port 372 in the form of an annular slit at annulus inner portion 370a. FIG. 12E is a sectional view of a feed injection annulus 370 having a plurality of feed injection ports 372 in the form of arcuate slits at annulus inner portion 370a. FIG. 12F is a sectional view of a feed injection annulus 370 having a plurality of feed injection ports 372 at annulus inner portion 370a, wherein feed injection ports 372 may be at least substantially circular. Although feed injection ports 372 in the embodiments of FIGS. 12D-12F are shown as being disposed substantially at the horizontal midline, M, of feed injection annulus 370 (see, e.g., FIG. 12G), other locations for feed injection ports 372 are also possible.

Figure 12G:
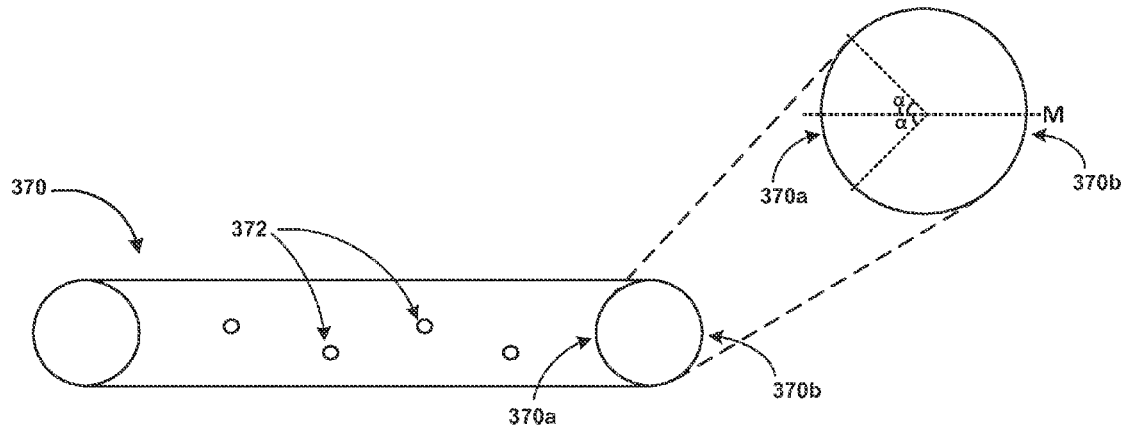

FIG. 12G is a sectional view of a feed injection annulus 370 having a plurality of feed injection ports 372. The enlarged projection at the right of FIG. 12G shows the horizontal midline, M, of feed injection annulus 370. In an embodiment, feed injection ports 372 may be disposed at various locations on annulus inner portion 370a spanning an angular range from 0 to 45° above or below the horizontal midline, M, i.e., a may be in the range from 0 to 45°. In an embodiment, each feed injection annulus 370 may have from two (2) to 50 feed injection ports 372, or from four (4) to 40 feed injection ports 372, or from six (6) to 30 feed injection ports 372. Feed injection annuli 370 are not limited to any one type of feed injection port 372, and a given feed injection annulus 370 may have two or more different types of feed injection ports 372 in various combinations.

In an embodiment, the first liquid comprising the central jet from the upper venturi outlet may comprise an external recirculation stream of the reactor vessel, and the second liquid may comprise a hydrocarbon feed. In an embodiment, the external recirculation stream may comprise reactor effluent in combination with added fresh ionic liquid catalyst, wherein the reactor effluent may have been cooled in a circulation loop before or after the addition of the fresh ionic liquid catalyst. In an embodiment, the ionic liquid catalyst may comprise, e.g., a chloroaluminate ionic liquid as described hereinbelow. In an embodiment, the hydrocarbon feed may comprise at least one of an olefin feed stream, an isoparaffin feed stream, and a mixed olefin/isoparaffin feed, for ionic liquid catalyzed alkylation, e.g., as also described hereinbelow.

Figure 13:
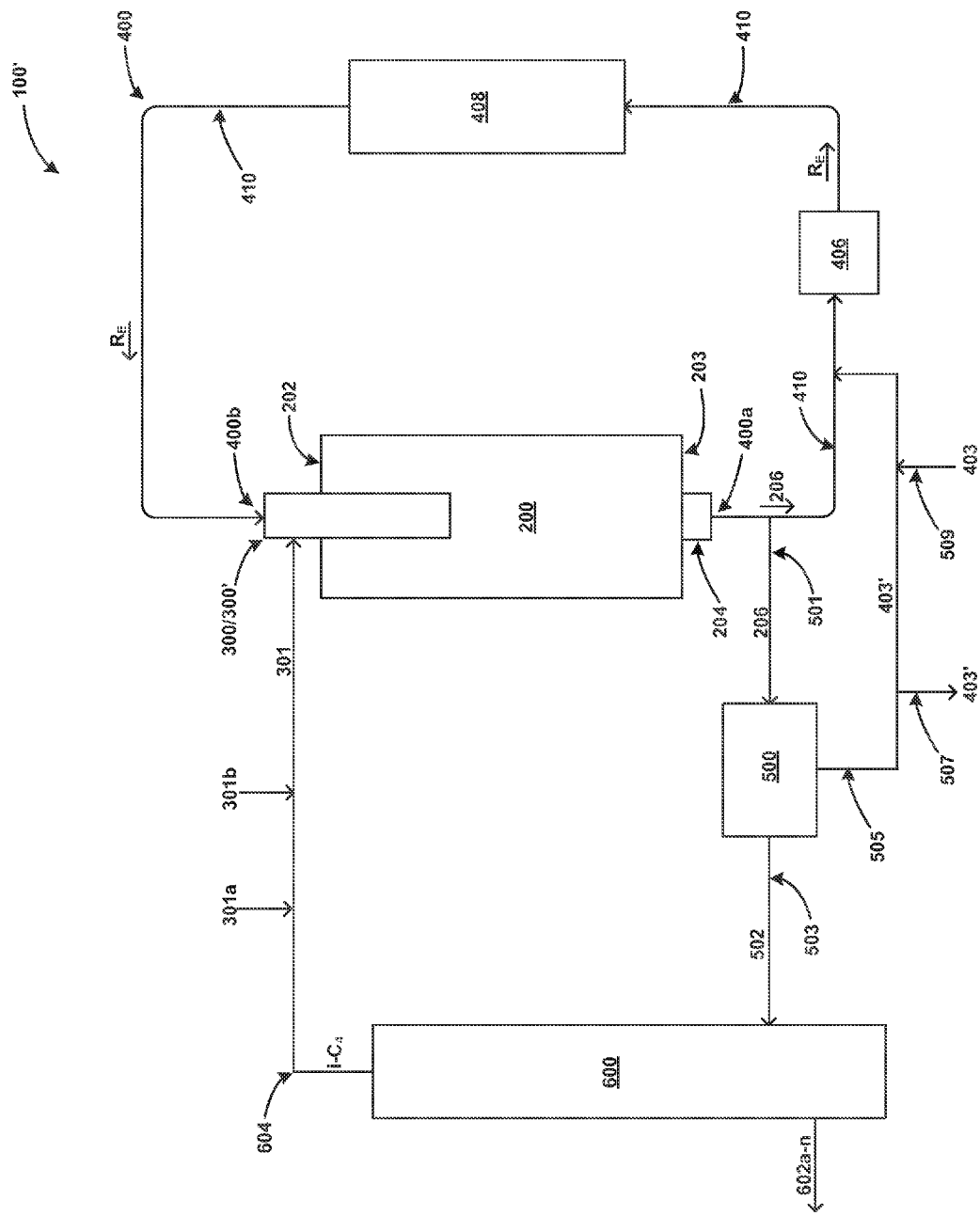
FIG. 13 schematically represents a system and process for ionic liquid catalyzed hydrocarbon conversion, according to another embodiment of the present invention.

FIG. 13 schematically represents a system and process for ionic liquid catalyzed hydrocarbon conversion, according to another embodiment. System 100' of FIG. 13 may comprise a reactor vessel 200 having a reactor vessel top 202, a reactor vessel base 203, and a vessel outlet 204; and one or more mixing devices 300/300' disposed at reactor vessel top 202 (see, for example, FIGS. 2-12G). System 100' may have elements and features in common with system 100 (see, for example, FIG. 1D). In reactor vessel 200, at least one isoparaffin and at least one olefin may be contacted with ionic liquid catalyst under ionic liquid alkylation conditions. Ionic liquid alkylation conditions, feedstocks, and ionic liquid catalysts that may be suitable for performing ionic liquid alkylation reactions are described, for example, hereinbelow.

In an embodiment, a process for ionic liquid catalyzed hydrocarbon conversion may include adding a co-catalyst, or a catalyst promoter, or both a catalyst promoter and a co-catalyst, to reactor vessel 200. In an embodiment, such a co-catalyst may comprise an alkyl chloride. A catalyst promoter for addition to the modular reactor may comprise a hydrogen halide, such as HCl. In an embodiment, a co-catalyst and/or a catalyst promoter may be fed to reactor vessel 200 via the hydrocarbon feed, or via the ionic liquid catalyst feed, or by separate direct injection into reactor vessel 200. The addition of co-catalyst(s) and/or catalyst promoter(s) to reactor vessel 200 is not shown in the Drawings. Various methods and techniques for introducing co-catalyst(s) and/or catalyst promoter(s) to reactor vessel 200 will be apparent to the skilled artisan.

System 100' may further comprise a circulation loop 400. Circulation loop 400 may comprise a first loop end 400a coupled to vessel outlet 204 and a second loop end 400b coupled to mixing device 300/300'. Circulation loop 400 may further comprise a circulation pump 406, and a heat exchanger 408. Circulation loop 400 may still further comprise at least one circulation loop conduit 410, e.g., for coupling components of circulation loop 400 to vessel outlet 204 and mixing device 300/300'.

System 100' may still further comprise an ionic liquid/hydrocarbon (IL/HC) separator 500 in fluid communication with circulation loop 400, and a fractionation unit 600 in fluid communication with IL/HC separator 500. Reactor effluent 206 may be withdrawn from reactor vessel 200 into circulation loop 400 via vessel outlet 204. A portion of the reactor effluent 206 may be fed from circulation loop 400, via a line 501, to IL/HC separator 500 for separation of the portion of reactor effluent into a hydrocarbon phase 502 and an ionic liquid phase 403'. Non-limiting examples of separation processes that can be used for such phase separation include coalescence, phase separation, extraction, membrane separation, and partial condensation. IL/HC separator 500 may comprise, for example, one or more of the following: a settler, a coalescer, a centrifuge, a cyclone, a distillation column, a condenser, and a filter. In an embodiment, IL/HC separator 500 may comprise a gravity based settler and a coalescer disposed downstream from the gravity based settler.

It can be seen from FIG. 13 that IL/HC separator 500 may be external to circulation loop 400. In an embodiment, circulation loop 400 may lack a unit or apparatus for phase separation of reactor effluent 206 or the external recirculation stream, $R_E$. Accordingly, reactor effluent 206 may be recirculated to reactor vessel 200 without any attempt to separate reactor effluent 206, or the external recirculation stream, within circulation loop 400. System 100' having IL/HC separator 500 external to circulation loop 400 allows IL/HC separator 500 to be smaller than that for a system in which a separator may be used for phase separation of 100% of the withdrawn reactor effluent within a hydrocarbon recycle loop.

The hydrocarbon phase 502 from IL/HC separator 500 may be fed via a line 503 to fractionation unit 600. The hydrocarbon phase from IL/HC separator 500 may comprise alkylate components (product), as well as unreacted components of hydrocarbon feed 301, including isobutane. The alkylate components may comprise, e.g., $C_5$-$C_{11}$ alkanes, such as $C_7$-$C_8$ isoparaffins. The hydrocarbon phase from IL/HC separator 500 may be fractionated via fractionation unit 600 to provide one or more products 602a-n and an isobutane fraction. In an embodiment, products 602a-n may comprise alkylate, n-butane, and propane. In an embodiment, fractionation unit 600 may comprise one or more distillation columns.

At least a portion of the isobutane stream from fractionation unit 600 may be recycled via a line 604 to mixing device(s) 300/300' and reactor vessel 200. In an embodiment, the recycle isobutane may be premixed with at least one of an olefin feed stream 301a and a make-up isobutane feed stream 301b to provide a mixed hydrocarbon feed 301 for injection into reactor vessel 200 via the one or mixing devices 300/300'.

The ionic liquid phase 403' from IL/HC separator 500 may be recycled to circulation loop 400 via a line 505. Make-up (fresh) ionic liquid catalyst 403 may be combined with the recycled ionic liquid catalyst via a line 509. The combined fresh and recycled ionic liquid catalyst may be injected into the reactor effluent within circulation loop 400 to provide an external recirculation stream, $R_E$, which may be cooled via heat exchanger 408. The cooled external recirculation stream may be recirculated to reactor vessel 200 via circulation loop 400 and mixing device(s) 300/300'. In an embodiment, the ionic liquid catalyst may be added to system 100' at a rate sufficient to maintain the overall ionic liquid catalyst volume in reactor vessel 200 in the range from 0.5 to 50 vol %, or from 1 to 10 vol %, or from 2 to 6 vol %.

In an embodiment, the ionic liquid phase 403' may be recycled to circulation loop 400 either directly or indirectly through a catalyst surge vessel (the latter not shown). In an embodiment, a portion of the ionic liquid phase 403' from IL/HC separator 500 may be purged or withdrawn to other vessels (not shown), via a line 507, for ionic liquid catalyst regeneration, e.g., as described hereinbelow.

Feedstocks for Ionic Liquid Catalyzed Alkylation

In an embodiment, feedstocks for ionic liquid catalyzed alkylation may comprise various olefin- and isoparaffin containing hydrocarbon streams in or from one or more of the following: a petroleum refinery, a gas-to-liquid conversion plant, a coal-to-liquid conversion plant, a naphtha cracker, a middle distillate cracker, a natural gas production unit, an LPG production unit, and a wax cracker, and the like.

Examples of olefin containing streams include FCC offgas, coker gas, olefin metathesis unit off-gas, polyolefin gasoline unit off-gas, methanol to olefin unit off-gas, FCC light naphtha, coker light naphtha, Fischer-Tropsch unit condensate, and cracked naphtha. Some olefin containing feed streams may contain at least one olefin selected from ethylene, propylene, butylenes, pentenes, and up to $C_{10}$ olefins, i.e., $C_2$-$C_{10}$ olefins, and mixtures thereof. Such olefin containing streams are further described, for example, in U.S. Pat. No. 7,572,943, the disclosure of which is incorporated by reference herein in its entirety.

Examples of isoparaffin containing streams include, but are not limited to, FCC naphtha, hydrocracker naphtha, coker naphtha, Fisher-Tropsch unit condensate, natural gas condensate, and cracked naphtha. Such streams may comprise at least one $C_4$-$C_{10}$ isoparaffin. In an embodiment, such streams may comprise a mixture of two or more isoparaffins. In a sub-embodiment, an isoparaffin feed to the alkylation reactor during an ionic liquid catalyzed alkylation process may comprise isobutane.

Paraffin Alkylation

In an embodiment, the alkylation of a mixture of hydrocarbons may be performed in a reactor vessel under conditions known to produce alkylate gasoline, and the reactor vessel may be referred to herein as an alkylation reactor or alkylation zone. The alkylation conditions in the alkylation reactor are selected to provide the desired product yields and quality. The alkylation reaction in the alkylation reactor is generally carried out in a liquid hydrocarbon phase, in a batch system, a semi-batch system, or a continuous system. The catalyst volume in the alkylation reactor may be in the range of 0.5 to 50 vol %, or from 1 to 10 vol %, or from 2 to 6 vol %. In an embodiment, vigorous mixing can be attained by using one or more mixing devices per reactor vessel, e.g., as described hereinabove, to provide contact between the hydrocarbon reactants and ionic liquid catalyst over a large surface area per unit volume of the reactor vessel. The alkylation reaction temperature can be in the range from −40° C. to 150° C., such as −20° C. to 100° C., or −15° C. to 50° C. The alkylation pressure can be in the range from atmospheric pressure to 8000 kPa. In an embodiment the alkylation pressure is maintained at a level at least sufficient to keep the reactants in the liquid phase. The residence time of reactants in the reactor can be in the range of a second to 60 hours.

In one embodiment, the molar ratio of isoparaffin to olefin in the alkylation reactor can vary over a broad range. Generally the molar ratio of isoparaffin to olefin is in the range of from 0.5:1 to 100:1. For example, in different embodiments the molar ratio of isoparaffin to olefin is from 1:1 to 50:1, from 1.1:1 to 10:1, or from 1.1:1 to 20:1. Lower isoparaffin to olefin molar ratios will tend to produce a higher yield of higher molecular weight alkylate products, and thus can be selected when operating the alkylation reactor in a distillate mode, such as described in U.S. Patent Publication No. US20110230692A1.

Other Hydrocarbon Conversion Processes

Systems as disclosed herein can be used for other hydrocarbon conversion processes using an acidic ionic liquid catalyst. Some examples of the hydrocarbon conversion processes include isomerization of $C_4$-$C_8$ paraffins wherein normal paraffins are converted to isoparaffins, oligomerization of $C_3$-$C_{30}$ olefins to produce higher molecular weight olefins, isomerization of $C_3$-$C_{30}$ olefins to shift the location of the double bond in the molecule (double bond isomerization) or shift the back-bone of the olefin molecules (skeletal isomerization), cracking of high molecular weight olefins and paraffins to low molecular paraffins and olefins, and alkylation of olefins with aromatics to form alkylaromatics.

Ionic Liquid Catalysts for Hydrocarbon Conversion Processes

In an embodiment, a catalyst for hydrocarbon conversion processes may be a chloride-containing ionic liquid catalyst comprised of at least two components which form a complex. A first component of the chloride-containing ionic liquid catalyst can comprise a Lewis Acid selected from components such as Lewis Acidic compounds of Group 13 metals, including aluminum halides, alkyl aluminum halides, gallium halides, alkyl gallium halides, indium halides, and alkyl indium halides (see International Union of Pure and Applied Chemistry (IUPAC), version 3, October 2005, for Group 13 metals of the periodic table). Other Lewis Acidic compounds, in addition to those of Group 13 metals, can also be used. In one embodiment the first component is aluminum halide or alkyl aluminum halide. For example, aluminum trichloride can be the first component of the chloride-containing ionic liquid catalyst.

A second component comprising the chloride-containing ionic liquid catalyst is an organic salt or mixture of salts. These salts can be characterized by the general formula $Q^+A^-$, wherein $Q^+$ is an ammonium, phosphonium, boronium, iodonium, or sulfonium cation and $A^-$ is a negatively charged ion such as $Cl^-$, $Br^-$, $ClO_4^-$, $NO_3^-$, $BF_4^-$, $BCl_4^-$, $PF_6^-$, $SbF_6^-$, $AlCl_4^-$, $TaF_6^-$, $CuCl_2^-$, $FeCl_3^-$, $HSO_3^-$, $RSO_3^-$ (wherein R is an alkyl group having from 1 to 12 carbon atoms), $SO_3CF_3^-$, and $_3^-$sulfurtrioxyphenyl. In one embodiment, the second component is selected from those having quaternary ammonium or phosphonium halides containing one or more alkyl moieties having from 1 to 12 carbon atoms, such as, for example, trimethylamine hydrochloride, methyltributylammonium halide, trialkylphosphonium hydrochloride, tetraalkylphosphonium chlorides, methyltrialkylphosphonium halide or substituted heterocyclic ammonium halide compounds, such as hydrocarbyl substituted pyridinium halide compounds, for example, 1-butylpyridinium halide, benzylpyridinium halide, or hydrocarbyl substituted imidazolium halides, such as for example, 1-ethyl-3-methyl-imidazolium chloride.

In one embodiment the chloride-containing ionic liquid catalyst is selected from the group consisting of hydrocarbyl substituted pyridinium chloroaluminate, hydrocarbyl substituted imidazolium chloroaluminate, quaternary amine chloroaluminate, trialkyl amine hydrogen chloride chloroaluminate, alkyl pyridine hydrogen chloride chloroaluminate, and mixtures thereof. For example, the chloride-containing ionic liquid catalyst can be an acidic haloaluminate ionic liquid, such as an alkyl substituted pyridinium chloroaluminate or an alkyl substituted imidazolium chloroaluminate of the general formulas A and B, respectively.

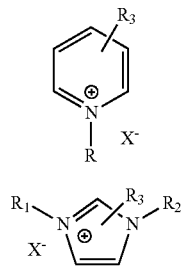

In the formulas A and B, R, $R_1$, $R_2$, and $R_3$ are H, methyl, ethyl, propyl, butyl, pentyl or hexyl group, and X is a chloroaluminate. In the formulas A and B, R, $R_1$, $R_2$, and $R_3$ may or may not be the same. In one embodiment the chloride-containing ionic liquid catalyst is N-butylpyridinium chloroaluminate. Examples of highly acidic chloroaluminates are $Al_2Cl_7^-$ and $Al_3Cl_{10}^-$.

In another embodiment the chloride-containing ionic liquid catalyst can have the general formula RR'R"NH$^+$ $Al_2Cl_7^-$, wherein R, R', and R" are alkyl groups containing from 1 to 12 carbons, and where R, R', and R" may or may not be the same.

In another embodiment the chloride-containing ionic liquid catalyst can have the general formula RR'R"R'"P$^+$ $Al_2Cl_7^-$, wherein R, R', R" and R'" are alkyl groups containing from 1 to 12 carbons, and wherein R, R', R" and R'" may or may not be the same.

The presence of the first component should give the chloride-containing ionic liquid a Lewis or Franklin acidic character. Generally, the greater the mole ratio of the first component to the second component, the greater is the acidity of the chloride-containing ionic liquid catalyst. The molar ratio of the first component (metal halide) to the second component (quaternary amine or quaternary phosphorus) is in the range of 2:1 to 1.1:1.

In one embodiment, the chloride-containing ionic liquid catalyst is mixed in the alkylation reactor with a hydrogen halide and/or an organic halide. The hydrogen halide or organic halide can boost the overall acidity and change the selectivity of the chloride-containing ionic liquid catalyst. The organic halide can be an alkyl halide. The alkyl halides that can be used include alkyl bromides, alkyl chlorides, alkyl iodides, and mixtures thereof. A variety of alkyl halides can be used. Alkyl halide derivatives of the isoparaffins or the olefins that comprise the feed streams in the alkylation process are good choices. Such alkyl halides include, but are not limited to, isopentyl halides, isobutyl halides, butyl halides (e.g., 1-butyl halide or 2-butyl halide), propyl halides and ethyl halides. Other alkyl chlorides or halides having from 1 to 8 carbon atoms can be also used. The alkyl halides can be used alone or in combination with hydrogen halide. The alkyl halide or hydrogen halide is fed to the unit by injecting the alkyl halide or hydrogen halide to the hydrocarbon feed, or to the ionic liquid catalyst, or to the alkylation reactor directly. The amount of HCl or alkylation chloride usage, the location of the injection, and the injection method may affect the amount of organic chloride side-product formation. The use of alkyl halides to promote hydrocarbon conversion by chloride-containing ionic liquid catalysts is taught in U.S. Pat. No. 7,495,144 and in U.S. Patent Publication No. 20100298620A1.

It is believed that the alkyl halide decomposes under hydrocarbon conversion conditions to liberate Bronsted acids or hydrogen halides, such as hydrochloric acid (HCl) or hydrobromic acid (HBr). These Bronsted acids or hydrogen halides promote the hydrocarbon conversion reaction. In one embodiment the halide in the hydrogen halide or alkyl halide is chloride. In one embodiment the alkyl halide is an alkyl chloride, for example t-butyl chloride. Hydrogen chloride and/or an alkyl chloride can be used advantageously, for example, when the chloride-containing ionic liquid catalyst is a chloroaluminate.

Ionic Liquid Catalyst Regeneration

As a result of use, ionic liquid catalysts become deactivated, i.e., lose activity, and may eventually need to be replaced. However, ionic liquid catalysts are expensive and replacement adds significantly to operating expenses. Thus it is desirable to regenerate the ionic liquid catalyst on-line and reuse it in the alkylation process. The regeneration of acidic ionic liquid catalysts is taught in U.S. Pat. No. 7,651,970, U.S. Pat. No. 7,674,739, U.S. Pat. No. 7,691,771, U.S. Pat. No. 7,732,363, and U.S. Pat. No. 7,732,364.

Alkylation processes utilizing an ionic liquid catalyst form by-products known as conjunct polymers. These conjunct polymers are highly unsaturated molecules and deactivate the ionic liquid catalyst by forming complexes with the ionic liquid catalyst. A portion of used ionic liquid catalyst from the alkylation reactor is sent to a regenerator reactor (not shown), which removes the conjunct polymer from the ionic liquid catalyst and recovers the activity of the ionic liquid catalyst. The regeneration reactor contains metal components that saturates the conjunct polymers and releases the saturated polymer molecules from the ionic liquid catalyst. The regeneration can be performed either in a stirred reactor or a fixed bed reactor. For ease of operation, a fixed bed reactor may be used, even though the fixed bed regenerator reactor is more susceptible to plugging from coking, deposits of corrosion products and decomposition products derived from feed contaminants. A guard bed vessel containing adsorbent material with appropriate pore size may be added before the regeneration reactor to minimize contaminants going into the regeneration reactor.

Product Separation and Finishing

The hydrocarbon effluent product from the reactor containing ionic liquid catalyst and hydrogen halide co-catalyst may contain trace amounts of hydrogen halides or organic halides or inorganic halides. When aluminum chloride containing catalyst is used, then trace amounts of HCl, organic chlorides and inorganic chlorides may be present in the reactor effluent. HCl and organic chlorides are preferred to be captured and recycled to the alkylation reactor. Inorganic chlorides such as corrosion products or decomposition product may be captured with a filter.

The separated hydrocarbon product may still contain trace amounts of HCl, organic chlorides and inorganic chlorides. Removal of HCl and inorganic chlorides from the product are typically done by caustic washing. Chloride selective adsorbent may be used to capture the residual chlorides. Organic chloride may be converted to HCl and organic hydrocarbon by hydrogenation, cracking or hot caustic treating. Treating of products for chloride reduction is taught, for example, in U.S. Pat. No. 7,538,256, U.S. Pat. No. 7,955,498, and U.S. Pat. No. 8,327,004.

For the purposes of this specification and appended claims, unless otherwise indicated, all numbers expressing quantities, percentages or proportions, and other numerical values used in the specification and claims, are to be understood as being modified in all instances by the term "about." Further-more, all ranges disclosed herein are inclusive of the endpoints and are independently combinable. Whenever a numerical range with a lower limit and an upper limit are disclosed, any number falling within the range is also specifically disclosed.

Any term, abbreviation or shorthand not defined is understood to have the ordinary meaning used by a person skilled in the art at the time the application is filed. The singular forms "a," "an," and "the," include plural references unless expressly and unequivocally limited to one instance.

All of the publications, patents and patent applications cited in this application are herein incorporated by reference in their entirety to the same extent as if the disclosure of each individual publication, patent application or patent was specifically and individually indicated to be incorporated by reference in its entirety.

The drawings are representational and may not be drawn to scale. Modifications of the exemplary embodiments disclosed above may be apparent to those skilled in the art in light of this disclosure. Accordingly, the invention is to be construed as including all structure and methods that fall within the scope of the appended claims. Unless otherwise specified, the recitation of a genus of elements, materials or other components, from which an individual component or mixture of components can be selected, is intended to include all possible sub-generic combinations of the listed components and mixtures thereof.

What is claimed is:

1. A system for ionic liquid catalyzed hydrocarbon conversion, the system comprising:
   a reactor vessel having a top; and
   a mixing device disposed at the top of the reactor vessel, wherein the mixing device comprises:
   an upper venturi having an axial outlet at the upper venturi distal end, the upper venturi distal end disposed within the reactor vessel,
   at least one feed injection array disposed within the reactor vessel, each said feed injection array coaxial with the upper venturi, and
   a lower venturi having an axial inlet at the lower venturi proximal end, the lower venturi proximal end disposed within the reactor vessel, wherein:
   the lower venturi inlet is spaced radially outward from the upper venturi outlet to define an inter-venturi channel between the upper venturi distal end and the lower venturi proximal end,
   the lower venturi is coaxial with the upper venturi,
   the mixing device is configured for projecting a central jet of a first liquid downward from the upper venturi outlet into the lower venturi, and
   each said feed injection array is configured for projecting second liquid toward an axis of the upper venturi.

2. The system according to claim 1, wherein the lower venturi inlet is disposed at the same elevation or about the same elevation as the upper venturi outlet.

3. The system according to claim 1, wherein:
   the lower venturi has a lower venturi constriction point,
   the at least one feed injection array comprises a single feed injection array, and
   the single feed injection array is disposed either at a first elevation of the mixing device or at a second elevation of the mixing device, and wherein:
   the first elevation is at the same elevation or about the same elevation as the lower venturi inlet, and
   the second elevation is at the same elevation or about the same elevation as the lower venturi constriction point.

4. The system according to claim 1, wherein the at least one feed injection array comprises:
   a first feed injection array disposed at a first elevation of the mixing device, and
   a second feed injection array disposed at a second elevation of the mixing device.

5. The system according to claim 4, wherein:
   the first elevation is at the same elevation or about the same elevation as the lower venturi inlet,
   the lower venturi has a lower venturi constriction point at an elevation below the lower venturi inlet, and
   the second elevation is at the same elevation or about the same elevation as the lower venturi constriction point.

6. The system according to claim 1, wherein each said feed injection array comprises from six (6) to 50 feed injection nozzles.

7. The system according to claim 1, further comprising:
   a circulation loop in fluid communication with the reactor vessel and the mixing device, the circulation loop having a first loop end coupled to a vessel outlet of the reactor vessel for withdrawing reactor effluent from the reactor vessel into the circulation loop, and the circulation loop further having a second loop end coupled to the mixing device, wherein the circulation loop comprises:
   an ionic liquid catalyst inlet configured for adding fresh ionic liquid catalyst to the reactor effluent, wherein the first liquid comprises the reactor effluent in combination with the fresh ionic liquid catalyst, and
   a heat exchanger configured for cooling the first liquid.

8. The system according to claim 7, further comprising:
   an ionic liquid/hydrocarbon separator in fluid communication with the circulation loop, wherein:
   the ionic liquid/hydrocarbon separator is external to the circulation loop,
   the system is configured for feeding a portion of the reactor effluent from the circulation loop to the ionic liquid/hydrocarbon separator, and
   the ionic liquid/hydrocarbon separator is configured for separating the portion of reactor effluent into an ionic liquid catalyst phase and a hydrocarbon phase.

9. The system according to claim 8, further comprising:
   a fractionation unit in fluid communication with the ionic liquid/hydrocarbon separator, wherein:
   the fractionation unit comprises one or more distillation columns, and
   the fractionation unit is configured for separating an alkylate product from the hydrocarbon phase.

10. The system according to claim 7, further comprising a static mixer in fluid communication with the heat exchanger and the mixing device.

11. The system according to claim 1,
    wherein:
    the system additionally comprises a circulation loop in fluid communication with the reactor vessel, and wherein:
    each said feed injection array comprises a plurality of feed injection nozzles;
    each said feed injection array is configured for projecting a plurality of lateral jets of a second liquid toward the axis of the upper venturi;
    the circulation loop comprises a heat exchanger in fluid communication with the reactor vessel;
    the heat exchanger is configured for cooling reactor effluent of the reactor vessel;
    the circulation loop is in fluid communication with the mixing device for delivering cooled reactor effluent to the mixing device; and
    the first liquid comprises the cooled reactor effluent.

12. The system according to claim 11, wherein:
the mixing device is configured for projecting the central jet axially downward from the upper venturi outlet into the lower venturi inlet, and
the axis of each said feed injection nozzle intersects the axis of the upper venturi at a common intersection at an elevation below the upper venturi outlet.

13. The system according to claim 11, wherein:
the lower venturi proximal end is disposed at the same elevation or about the same elevation as the upper venturi distal end,
the at least one feed injection array is at the same elevation or about the same elevation as the lower venturi proximal end, and
the plurality of feed injection nozzles terminate at the same radial location or about the same radial location as the perimeter of the upper venturi outlet.

14. The system according to claim 1, wherein:
the system further comprises a vessel outlet and a circulation loop in fluid communication with the vessel outlet;
the mixing device is in fluid communication with the reactor vessel;
the system is configured for withdrawing a reactor effluent from the reactor vessel via the vessel outlet into the circulation loop;
the circulation loop comprises a heat exchanger configured for cooling withdrawn reactor effluent;
the circulation loop is configured for recirculating at least a portion of the withdrawn reactor effluent to the mixing device to provide an external recirculation stream to the reactor vessel;
the external recirculation stream comprises the withdrawn reactor effluent;
the upper venturi has an axial upper venturi inlet at the upper venturi proximal end and is in fluid communication with the circulation loop for receiving the external recirculation stream at the axial upper venturi inlet;
the upper venturi is configured for projecting a central jet of the external recirculation stream axially downward from the upper venturi outlet and;
each said feed injection array is configured for simultaneously projecting a plurality of lateral jets of hydrocarbon feed toward the central jet of the external recirculation stream.

15. The system according to claim 14, wherein:
the lower venturi inlet is disposed at the same elevation or about the same elevation as the upper venturi outlet,
each of the lower venturi inlet and the upper venturi outlet is at least substantially circular,
the inter-venturi channel is at least substantially annular, and
the inter-venturi channel is configured for circulation therethrough of an internal recirculation stream of the reactor vessel.

16. The system according to claim 1,
wherein the feed injection array comprises a feed injection annulus having at least one feed injection port.

17. The system according to claim 16, wherein the at least one feed injection port comprises an annular slit in an inner portion of the feed injection annulus.

18. The system according to claim 16, wherein the feed injection annulus has from two (2) to 50 of said feed injection ports.

19. The system according to claim 18, wherein said feed injection ports are symmetrically arranged on an inner portion of the feed injection annulus.

20. The system according to claim 16, wherein the second liquid is projected as a jet from each said feed injection port.

21. The system according to claim 16, wherein:
the feed injection annulus is coaxial with the upper venturi, and
the system is configured such that at least one jet of the second liquid collides with the central jet.

22. The system according to claim 16, wherein the feed injection annulus is disposed at the same elevation or about the same elevation as the lower venturi inlet.

23. The system according to claim 16, wherein the lower venturi inlet is disposed at the same elevation or about the same elevation as the upper venturi outlet.

24. The system according to claim 16, further comprising:
a circulation loop in fluid communication with the reactor vessel and the mixing device, the circulation loop having a first loop end coupled to a vessel outlet of the reactor vessel for withdrawing reactor effluent from the reactor vessel into the circulation loop, and the circulation loop further having a second loop end coupled to the mixing device, wherein the circulation loop comprises:
an ionic liquid catalyst inlet configured for adding fresh ionic liquid catalyst to the reactor effluent, and
a heat exchanger configured for cooling the first liquid, wherein the first liquid comprises the reactor effluent in combination with the fresh ionic liquid catalyst, and the second liquid comprises a hydrocarbon feed.

25. The system according to claim 24, further comprising:
an ionic liquid/hydrocarbon separator in fluid communication with the circulation loop, wherein:
the ionic liquid/hydrocarbon separator is external to the circulation loop,
the system is configured for feeding a portion of the reactor effluent from the circulation loop to the ionic liquid/hydrocarbon separator, and
the ionic liquid/hydrocarbon separator is configured for separating the portion of reactor effluent into an ionic liquid catalyst phase and a hydrocarbon phase.

26. The system according to claim 25, further comprising:
a fractionation unit in fluid communication with the ionic liquid/hydrocarbon separator, wherein:
the fractionation unit comprises one or more distillation columns, and
the fractionation unit is configured for separating an alkylate product from the hydrocarbon phase.

27. The system according to claim 1, wherein each said feed injection array comprises a plurality of feed injection nozzles.

28. The system according to claim 27, wherein the plurality of feed injection nozzles of each said feed injection array are symmetrically arranged.

29. The system according to claim 27, wherein the axis of each said feed injection nozzle intersects the axis of the upper venturi at an angle, $\theta$, in the range from 20° to 90°.

30. The system according to claim 27, wherein the axis of each said feed injection nozzle intersects the axis of the upper venturi at an angle, $\theta$, in the range from 80° to 90°.

31. The system according to claim 27, wherein each said feed injection array is configured for projecting a plurality of lateral jets of the second liquid toward the axis of the upper venturi.

32. The system according to claim 31, wherein:
each said feed injection nozzle projects one of said lateral jets, and
each said feed injection nozzle terminates at the same radial location or about the same radial location as the perimeter of the upper venturi outlet.

33. The system according to claim 31, wherein each said feed injection nozzle terminates at a location radially inward from the perimeter of the upper venturi outlet such that the central jet collides with at least a terminal portion of each said feed injection nozzle.

34. The system according to claim 31, wherein:
the system is configured such that each said lateral jet collides with the central jet, and
the system is further configured such that a first liquid linear velocity of the central jet is at least substantially equal to a second liquid linear velocity of each said lateral jet.

35. The system according to claim 1, wherein the inter-venturi channel is configured for circulation therethrough of an internal recirculation stream of the reactor vessel.

36. A process for ionic liquid catalyzed hydrocarbon conversion, comprising:
a) withdrawing reactor effluent from a reactor vessel, the reactor effluent comprising unreacted hydrocarbons from a hydrocarbon feed;
b) adding ionic liquid catalyst to the reactor effluent to provide an external recirculation stream;
c) introducing the external recirculation stream into a mixing device, the mixing device in fluid communication with the reactor vessel, wherein the mixing device comprises an upper venturi having an axial outlet at the upper venturi distal end and a lower venturi having an axial inlet at the lower venturi proximal end;
d) projecting a central jet of the external recirculation stream downward from the upper venturi outlet into the lower venturi;
e) circulating an internal recirculation stream through the lower venturi via an inter-venturi channel that is provided by the lower venturi inlet being spaced radially outward from the upper venturi; and
f) concurrently with the projecting of the central jet, projecting a hydrocarbon feed toward the central jet such that the hydrocarbon feed collides with the central jet, wherein:
the upper venturi distal end and the lower venturi proximal end are disposed within the reactor vessel, and
the lower venturi is coaxial with the upper venturi.

37. The process according to claim 36, wherein:
the central jet comprises an ionic liquid/hydrocarbon emulsion comprising droplets of the ionic liquid catalyst, and
step f) comprises contacting the hydrocarbon feed with the ionic liquid catalyst under alkylation conditions to provide an alkylate product.

38. The process according to claim 37, wherein:
the ionic liquid catalyzed hydrocarbon conversion comprises paraffin alkylation,
the hydrocarbon feed comprises at least one $C_2$-$C_{10}$ olefin and at least one $C_4$-$C_{10}$ isoparaffin,
the ionic liquid catalyst comprises a chloroaluminate ionic liquid, and
the alkylation conditions comprise a temperature in the range from −40° C. to 150° C., and a pressure in the range from atmospheric pressure to 8000 kPa.

39. The process according to claim 36, wherein:
the mixing device further comprises a feed injection array disposed within the reactor vessel,
the feed injection array comprises a plurality of feed injection nozzles, and
step f) comprises projecting the hydrocarbon feed toward the central jet via the feed injection nozzles.

40. The process according to claim 36, wherein:
the mixing device further comprises a feed injection annulus disposed within the reactor vessel, the feed injection annulus having at least one feed injection port, and
step f) comprises projecting the hydrocarbon feed toward the central jet via the at least one feed injection port.

41. The process according to claim 36, wherein the central jet comprises an ionic liquid/hydrocarbon emulsion comprising droplets of the ionic liquid catalyst having a diameter in the range from 1-1000 microns.

42. The process according to claim 36, wherein the ionic liquid catalyzed hydrocarbon conversion is selected from the group consisting of: paraffin alkylation, paraffin isomerization, olefin oligomerization, cracking of olefins or paraffins, and aromatic alkylation.

43. The process according to claim 36, further comprising:
g) feeding a portion of the reactor effluent to an ionic liquid/hydrocarbon separator;
h) via the ionic liquid/hydrocarbon separator, separating the portion of reactor effluent into an ionic liquid catalyst phase and a hydrocarbon phase; and
i) via a fractionation unit, separating an alkylate product from the hydrocarbon phase.

* * * * *